(12) United States Patent  
Boudreau et al.

(10) Patent No.: US 10,775,304 B2
(45) Date of Patent: Sep. 15, 2020

(54) FLUORESCENT NANOSENSORS AND USES THEREOF

(71) Applicant: UNIVERSITÉ LAVAL, Quebec (CA)

(72) Inventors: Denis Boudreau, Sainte-Foy (CA); Jérémie Asselin, Pintendre (CA); Marie-Christine Dorais, Quebec (CA)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 15/312,886

(22) PCT Filed: May 25, 2015

(86) PCT No.: PCT/CA2015/000337
§ 371 (c)(1),
(2) Date: Jul. 28, 2017

(87) PCT Pub. No.: WO2015/176168
PCT Pub. Date: Nov. 26, 2015

(65) Prior Publication Data
US 2017/0191935 A1 Jul. 6, 2017

Related U.S. Application Data

(60) Provisional application No. 62/002,522, filed on May 23, 2014, provisional application No. 62/013,347, filed on Jun. 17, 2014.

(51) Int. Cl.
G01N 21/69 (2006.01)
G01N 21/64 (2006.01)
(Continued)

(52) U.S. Cl.
CPC ....... *G01N 21/6428* (2013.01); *G01N 21/645* (2013.01); *G01N 33/582* (2013.01);
(Continued)

(58) Field of Classification Search
CPC .......... G01N 21/6489; G01N 27/4146; G01N 21/6428; G01N 29/022; G01N 33/54373;
(Continued)

(56) References Cited

U.S. PATENT DOCUMENTS

2005/0281884 A1* 12/2005 Adair ................. A61K 49/0041
424/489
2006/0074075 A1 4/2006 Hadida-Ruah et al. .....................
514/217.01
(Continued)

FOREIGN PATENT DOCUMENTS

WO WO 2011/042564 4/2011

OTHER PUBLICATIONS

Badruddoza et al., "Beta-cyclodextrin conjugated magnetic, fluorescent silica core-shell nanoparticles for biomedical applications," 2013, Carbodydrate Polymers, vol. 95, pp. 449-457. (Year: 2013).*

(Continued)

*Primary Examiner* — Kiho Kim
(74) *Attorney, Agent, or Firm* — Norton Rose Fulbright US LLP

(57) ABSTRACT

Fluorescent nanosensors for extracellular ion concentration measurements are disclosed herein. More specifically, a fluorescent nanosensor for extracellular ion measurements comprising a photoluminescent nanostructure disposed on a substrate surface is disclosed. The photoluminescent nanostructure comprises a fluorescent metallic core-silica shell containing nanoparticle, wherein the fluorescent silica shell comprises a fluorophore dispersed therein. The nanosensor emits a fluorescence emission in function of the extracellular ion concentration.

26 Claims, 14 Drawing Sheets

(51) Int. Cl.
G01N 33/58 (2006.01)
B82Y 15/00 (2011.01)
(52) U.S. Cl.
CPC ............ G01N 33/587 (2013.01); B82Y 15/00 (2013.01); G01N 2021/6439 (2013.01); Y10S 977/92 (2013.01)
(58) Field of Classification Search
CPC ........... G01N 33/5438; G01N 27/4145; G01N 2021/6432; G01N 2291/011; G01N 2291/014; G01N 2291/0255; G01N 2291/0256; G01N 2291/0423; G01N 2291/0426; G01N 2021/6439; G01N 33/587
See application file for complete search history.

(56) References Cited

U.S. PATENT DOCUMENTS

| | | | |
|---|---|---|---|
| 2008/0118912 A1* | 5/2008 | Dickson | A61K 49/0065 435/6.12 |
| 2009/0004670 A1 | 1/2009 | Zhang et al. | |
| 2009/0022766 A1 | 1/2009 | Geddes | |
| 2009/0068755 A1* | 3/2009 | Steeves | B82Y 5/00 436/172 |
| 2010/0151206 A1 | 6/2010 | Wu et al. | 428/158 |
| 2012/0282632 A1* | 11/2012 | Chiu | G01N 33/582 435/7.23 |
| 2013/0210047 A1 | 8/2013 | Tang et al. | |
| 2015/0268244 A1* | 9/2015 | Cho | G01N 15/1429 435/7.23 |

OTHER PUBLICATIONS

Eom et al., "Core-size-dependent properties of CdSe/CdS core/shell QDs," 2013, Materials Letters, vol. 99. pp. 14-17. (Year: 2013).*
Yin et al., "Fluorescence enhancement of Ru(bpy)32+ by core-shell Ag@SiO2 nanoconnposites," 2013, Journal of Alloys and Compounds, vol. 581, pp. 6-10. (Year: 2013).*
Yao et al., "Fabrication of Fe3O4/SiO2 core/shell nanoparticles attached to graphene oxide and its use as an adsorbent," 2012, Journal of Colloid and Interface Science, vol. 379, pp. 20-26. (Year: 2012).*
Aslan et al., "Metal-enhanced fluorescence: an emerging tool in biotechnology," Current Opinion in Biotechnology. 16: 2005, 55-62.
Bai et al., "Fluorescent pH Sensor Based on Ag@SiO$_2$ Core-Shell Nanoparticle," ACS Appl Mater Interfaces, 5: 2013, 5856-5860.
Bradburne et al., "Cytotoxicity of Quantum Dots Used for in Vitro Cellular Labeling: Role of QD Surface Ligand, Delivery Modality, Cell Type, and Direct Comparison to Organic Fluorophores," Bioconjugate Chem, 24: 2013, 1570-1583.
Brouard et al., "Direct molecular detection of SRY gene from unamplified genomic DNA by metal-enhanced fluorescence and FRET," Anal Methods, 5(24): 2013, 6896-6899.
Cash et al., "Phosphorescent Nanosensors for in Vivo Tracking of Histamine Levels." Anal Chem. 85: 2013, 6312-6318.
Chandran et al., "Tunable surface modification of silica nanoparticles through 'click' chemistry," Current Science, 95(9): 2008, 1327-1333.
Deng et al., "Ultrabright Eu-Doped Plasmonic Ag@SiO$_2$ Nanostructures: Time-gated Bioprobes with Single Particle Sensitivity and Negligible Background," Adv Mater, 23: 2011, 4649-4654.
Devaraj et al., "Copper Catalyzed Azide-Alkyne Cycloadditions on Solid Surfaces: Applications and Future Directions," QSAR Comb Sci, 26(11-12): 2007, 1253-1260.
Franck et al., "Measurement of intracellular pH in cultured cells by flow cytometry with BCECF-AM," Journal of Biotechnology, 46: 1996, 187-195.
Fried et al., "Immobilizing glycopyranose on mesoporous silica via "click-chemistry" for borate adsorption," Microporous and Mesoporous Materials, 147: 2012, 5-9.
Grienberger et al., "Imaging Calcium in Neurons," Neuron, 73: 2012, 862-885.
Harjes et al., "Ion-Selective Optodes Measure Extracellular Potassium Flux in Excitable Cells," Macromol Rapid Commun, 31: 2010, 217-221.
Huang et al., ""Click" Grafting of High Loading of Polymers and Monosaccharides on Surface of Ordered Mesoporous Silica, Langmuir, 26(4): 2010, 2688-2693.
Klonis et al., "Spectral Proper of the Prototropic Forms of Fluorescein in Aqueous Solution," Journal of Fluorescence, 6(3): 1996, 147-157.
Lacroix et al., "Molecular Bases for the Asynchronous Activation of Sodium and Potassium Channels Required for Nerve Impulse Generation," Neuron, 79: 2013, 651-657.
Lakowicz, "Radiative decay engineering 5: inetal-enhanced fluorescence and plasmon emission," Anal Biochem, 337: 2005, 171-194.
Leclerc et al., "Bioaccumulation of Nanosilver by Chlamydomonas reinhardtii—Nanoparticle or the Free Ion?", Environ Sci Technol, 48: 2014, 358-364.
Lee et al., "Metal-Enhanced Fluorescence to Quantify Bacterial Adhesion," Adv Mater, 23: 2011, H101-H104.
Lin et al., "Site-Specific Protein Modification through Cu$^1$-Catalyzed 1,2,3-Triazole Formation and Its Implementation in Protein Microarray Fabrication," Angew Chem, 118: 2006, 4392-4396.
Lin et al., "Surface Modification of Magnetic Nanoparticles via a Cu(I)-Catalyzed Alkyne-azide [2+3] Cycloaddition," Org Lett, 9: 2007, 2131-2134.
Magnan et al., "Indium@silica core-shell nanoparticles as plasmonic enhancers of molecular luminescence in the UV region," Chem Commun, 49: 2013, 9299-9301.
Nakata et al., "Synthesis and photophysical properties of new SNARF derivatives as duel emission pH sensors," Bioorg Med Chem Lett, 21: 2011, 1663-1666.
Nath et al., "A Colorimetric Gold Nanoparticle Sensor to Interrogate Biomolecular Interactions in Real Time on a Surface", Anal Chem, 74: 2002, 504-509.
O'leary et al., "Role of voltage-gated sodium, potassium and calcium channels in the development of cocaine-associated cardiac arrhythmias," Br J Clin Pharmacol, 69: 2010, 427-442.
Prakash et al., "Click" Modification of Silica Surfaces and Glass Microfluidic Channels, Anal Chem, 79: 2007, 1661-1667.
Rainville et al., "Controlled synthesis of low polydispersity Ag@SiO$_2$ core-shell nanoparticles for use in plasmonic applications," RSC Adv, 3: 2013, 13953-13960.
Rodionov et al., "Mechanism of the Ligand-Free Cu$^1$-Catalyzed Azide-Alkyne Cycloaddition Reaction," Angew Chem, 117: 2005, 2250-2255.
Rostovtsev et al., "A Stepwise Huisgen Cycloaddition Process: Copper(I)-Catalyzed Regioselective "Ligation" of Azides and Terminal Alkynes," Angew Chem, 114: 2002, 2708-2711.
Tian et al., "A fluorescent colorimetric pH sensor and the influences of matrices on sensing performances," Sensors and Actuators B—Chem, 188: 2013, 1-10.
Tiedemann et al., "Reprotoxicity of gold, silver, and gold-silver allow nanoparticles on mammalian gametes," Analyst, 139: 2014, 931-942.
Tovmachenko et al., "Fluorescence Enhancement by Metal-Core/Silica-Shell Nanoparticles," Adv Mater, 18: 2006, 91-95.
Viger et al., "Plasmon-Enhanced Resonance Energy Transfer from a Conjugated Polymer to Fluorescent Multilayer Core-Chell Nanoparticles: A Photophysical Study," J Phys Chem C, 115: 2011, 2974-2981.
Viger et al., "Reduction of Self-Quenching in Fluorescent Silica-Coated Silver Nanoparticles," Plasmonics, 3: 2008, 33-40.
Webb et al., "Dysregulated pH: a perfect storm for cancer progression," Nat Rev Cancer, 11: 2011, 671-677.
Wieder et al., "Measurement of Intracellular pH Using Flow Cytometry With Carboxy-SNARF-1," Cytometry, 14: 1993. 916-921.

(56) References Cited

OTHER PUBLICATIONS

Yang et al., "Core-shell Ag@SiO$_2$@mSiO$_2$ mesoporous nanocarriers for metal-enhanced fluorescence," *Chem Commun*, 47: 2011, 11681-11620.

Yang et al., "Inhibition of Beta-Amyloid Peptide Aggregation by Multifunctional Carbazole-Based Fluorophores," *Angew Chem Int Ed*, 51: 2012, 1804-1810.

Extended European Search Report issued in PCT/CA2015/000337, dated Jan. 15, 2018.

Zhou, et al. "1,3-Dipolar Cycloaddition as a General Route for Functionalization of Fe$_3$O$_4$ Nanoparticles," *Nanotechnology*, 19(17), p. 179802. (2009).

International Search Report for PCT/CA2015/000337 dated Aug. 24, 2015.

\* cited by examiner

FLUORESCENT NANOSENSORS AND USES THEREOF

CROSS-REFERENCE TO RELATED APPLICATIONS

The present application is a national phase application under 35 U.S.C. § 371 of International Application No. PCT/CA2015/000337 filed May 25, 2015, which claims the benefit of priority from U.S. Provisional Applications Nos. 62/002,522 and 62/013,347 filed on May 23, 2014 and Jun. 17, 2014 respectively, the contents of which are incorporated herein by reference in their entirety.

FIELD

The present disclosure broadly relates to fluorescent nanosensors. More specifically but not exclusively, the present disclosure relates to fluorescent nanosensors for in-vitro and in-vivo extracellular ion concentration measurements. The present disclosure also relates to a process for grafting the fluorescent nanosensors on a substrate.

BACKGROUND

Quantitative measurements of physiological ions at proximity of biological membranes are crucial methods to investigate metabolic processes and to identify unhealthy cells. In fact, the variation in concentration gradients is still predominant in medical studies—pH in cancer cells[1], calcium ions and neurotransmitters in neurons[2,3], or sodium and potassium in various excitable cells.[4-6] Current methods focus mainly on fluorescent markers to react to these environmental changes by a modification in their emissive properties in different conditions. However, these markers have often shown a certain cytotoxicity[7,8], which limits their use for long-term analyses and raises many questions concerning the stress induced during these tests.

Because of its intrinsic analytical advantages—namely, minimal photophysical stress induction, high sensitivity to minute signal variation, and adaptability on multiple biomedical platforms—fluorescence spectroscopy continues to be a dominant technology in various fields. Moreover, it has been found that dipole-dipole coupling with conductive electrons of a metallic surface can improve the optical properties of organic fluorophores.[9-11] This collective oscillation, termed "surface plasmon", is induced by specific electromagnetic wavelengths and can be localized on nanometric conductive domains. Metal-enhanced fluorescence (MEF) is therefore influenced by the position of the molecule in the resulting electric field, and this distance dependency is well documented on metallic surfaces with a thin silica spacer.[9] In recent years, the development of MEF core-shell nanoparticles has been the subject of multiple studies and is now a whole theme in itself.[12-15] Easily dispersible in most solvents, various diagnosis applications have arisen from this type of highly-luminescent nanoparticular architecture.[16,17]

Although showing multiple advantages for homogeneous sensing in aqueous solutions, core-shell nanoparticles have also been shown to be functional on two-dimensional substrates to create fluorescent chip-based sensors with a higher surface ratio than continuous metallic films. The covalent grafting of nanoparticular sensors on transparent matrices, e.g. silica coverslip, is particularly valuable for bio-characterization using fluorescence microscopes. This methodology allows for multiple emitters on the same device without undesirable FRET and better control of the fluorophore-plasmonic core distance, whereas deposited metal surfaces are limited in these aspects. Furthermore, the development of planar devices allows for high-throughput and rapid analysis of liquids by microfluidic spectrofluorimetry[18], while also inhibiting the formation of plasmonic aggregates, which results in a highly homogeneous fluorescent biochip.

The grafting of proteins on the surface of metallic nanoparticles by click chemistry has been described in the literature.[19] The "click" method has also been used on lamellar silica substrates in order to add antibodies and polysaccharides for surface sensing.[20-23]

The present disclosure refers to a number of documents, the contents of which are herein incorporated by reference in their entirety.

SUMMARY

The present disclosure broadly relates to fluorescent nanosensors. In one aspect, the present disclosure includes a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration. In a further aspect, the present disclosure includes a fluorescent nanosensor for extracellular pH measurements, the fluorescent nanosensor comprising a photoluminescent nanostructure disposed on a substrate surface, wherein the nanosensor emits a fluorescence emission in function of the extracellular pH.

In an embodiment of the present disclosure, the photoluminescent nanostructure comprises a fluorescent metallic core-silica shell containing nanoparticle, wherein the fluorescent silica shell comprises a fluorophore dispersed therein.

In an embodiment of the present disclosure, the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein; and wherein the fluorescent silica shell is functionalized with a first functionalized silane reagent having a first functionality.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein; and wherein the fluorescent silica shell is functionalized with a first functionalized silane reagent having a first functionality.

In one aspect of the present disclosure, the substrate surface is functionalized with a functionalized silane reagent comprising a functionality that is complementary to the functionality of the functionalized silica shell such that these functionalities can undergo a cycloaddition reaction resulting in the grafting of the nanostructure on the substrate surface. In an embodiment of the present disclosure, the cycloaddition reaction is selected from [4+2] cycloadditions and [3+2] cycloadditions. In one aspect of the present disclosure, the first and second functionalized silane reagents have a general formula independently chosen from $(R^1O)_3Si-R$ or $(R^1O)_3Si-R'$, wherein R' is an alkyl group and wherein R and R' are complementary groups comprising a functionality such that R and R' are capable of forming a cycloadduct resulting in the grafting of the nanoparticle on the substrate.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh. In an aspect of the present disclosure, the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh. In an aspect of the present disclosure, the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle, wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh. In an aspect of the present disclosure, the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$. In an aspect of the present disclosure, the fluorophore is selected from Oregon Green™, SBFI, PBFI, Fura Red™, CoroNa™ Green, FluoZin™, Newport Green™, Calcium Green™, Fluo-3, Magnesium Green™, Calcium Orange™, Calcium Crimson™, TSQ, SNARF™, SNARF™ derivatives, MQAE, Phen Green™, SPQ, fluorescein 5(6)-isothiocyanate, EiTC, BCECF and DNA aptamers.

In an embodiment, the present disclosure relates to a fluorescent nanosensor for extracellular ion concentration measurements, the fluorescent nanosensor comprising a photoluminescent nanostructure disposed on a substrate surface, wherein the nanosensor emits a fluorescence emission in function of the extracellular ion concentration; wherein the photoluminescent nanostructure comprises a fluorescent metallic core-silica shell containing nanoparticle comprising a spacer shell interposed between the metallic core and the fluorescent silica shell, and wherein the fluorescent silica shell comprises a fluorophore dispersed therein; and wherein the fluorescent silica shell is functionalized with a first functionalized silane reagent having a first functionality. In an aspect of the present disclosure, the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$. In an aspect of the present disclosure, the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh. In an aspect of the present disclosure, the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$. In an aspect of the present disclosure, the fluorophore is selected from Oregon Green™, SBFI, PBFI, Fura Red™, CoroNa™ Green, FluoZin™, Newport Green™, Calcium Green™, Fluo-3, Magnesium Green™, Calcium Orange™, Calcium Crimson™, TSQ, SNARF™, SNARF™ derivatives, MQAE, Phen Green™, SPQ, fluorescein 5(6)-isothiocyanate, EiTC, BCECF and DNA aptamers.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate;

wherein the cycloaddition reaction is selected from [4+2] cycloadditions and [3+2] cycloadditions.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the fluorophore is selected from Oregon Green™, SBFI, PBFI, Fura Red™, CoroNa™ Green, FluoZin™, Newport Green™, Calcium Green™, Fluo-3, Magnesium Green™, Calcium Orange™, Calcium Crimson™, TSQ, SNARF™, SNARF™ derivatives, MQAE, Phen Green™, SPQ, fluorescein 5(6)-isothiocyanate, EiTC, BCECF and DNA aptamers.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the ion is selected $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure includes a process for preparing a fluorescent nanosensor for extracellular ion concentration measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$.

In an embodiment, the present disclosure includes a process for preparing a fluorescent nanosensor for extracellular ion concentration measurements, the process comprising:

treating a nanoparticle with a silane reagent under conditions to provide a silica shell containing nanoparticle;

treating the silica shell containing nanoparticle with a second silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an embodiment, the present disclosure includes a process for preparing a fluorescent nanosensor for extracellular ion concentration measurements, the process comprising:
- treating a nanoparticle with a silane reagent under conditions to provide a silica shell containing nanoparticle;
- treating the silica shell containing nanoparticle with a second silane reagent in the presence of a fluorophore under conditions to provide a fluorescent silica shell containing nanoparticle, wherein the fluorescent silica shell comprises the fluorophore dispersed therein;
- reacting the fluorescent silica shell containing nanoparticle with a first functionalized silane reagent having a first functionality, under conditions to provide a functionalized nanoparticle comprising a functionalized silica shell; and
- reacting the functionalized nanoparticle with a substrate functionalized with a second functionalized silane reagent, the second functionalized silane reagent comprising a second functionality complementary to the first functionality;
- wherein the functionalized nanoparticle undergoes a cycloaddition reaction with the functionalized substrate to provide the fluorescent nanosensor;
- wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

In an embodiment, the present disclosure includes a process for preparing a fluorescent nanosensor for extracellular ion concentration measurements, the process comprising:
- treating a nanoparticle with a silane reagent under conditions to provide a silica shell containing nanoparticle;
- treating the silica shell containing nanoparticle with a second silane reagent in the presence of a fluorophore under conditions to provide a fluorescent silica shell containing nanoparticle, wherein the fluorescent silica shell comprises the fluorophore dispersed therein;
- reacting the fluorescent silica shell containing nanoparticle with a first functionalized silane reagent having a first functionality, under conditions to provide a functionalized nanoparticle comprising a functionalized silica shell; and
- reacting the functionalized nanoparticle with a substrate functionalized with a second functionalized silane reagent, the second functionalized silane reagent comprising a second functionality complementary to the first functionality;
- wherein the functionalized nanoparticle undergoes a cycloaddition reaction with the functionalized substrate to provide the fluorescent nanosensor;
- wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate;
- wherein the cycloaddition reaction is selected from [4+2] cycloadditions and [3+2] cycloadditions.

In an embodiment, the present disclosure includes a process for preparing a fluorescent nanosensor for extracellular ion concentration measurements, the process comprising:
- treating a nanoparticle with a silane reagent under conditions to provide a silica shell containing nanoparticle;
- treating the silica shell containing nanoparticle with a second silane reagent in the presence of a fluorophore under conditions to provide a fluorescent silica shell containing nanoparticle, wherein the fluorescent silica shell comprises the fluorophore dispersed therein;
- reacting the fluorescent silica shell containing nanoparticle with a first functionalized silane reagent having a first functionality, under conditions to provide a functionalized nanoparticle comprising a functionalized silica shell; and
- reacting the functionalized nanoparticle with a substrate functionalized with a second functionalized silane reagent, the second functionalized silane reagent comprising a second functionality complementary to the first functionality;
- wherein the functionalized nanoparticle undergoes a cycloaddition reaction with the functionalized substrate to provide the fluorescent nanosensor;
- wherein the fluorophore is selected from Oregon Green™, SBFI, PBFI, Fura Red™, CoroNa™ Green, FluoZin™, Newport Green™, Calcium Green™, Fluo-3, Magnesium Green™, Calcium Orange™, Calcium Crimson™, TSQ, SNARF™, SNARF™ derivatives, MQAE, Phen Green™, SPQ, fluorescein 5(6)-isothiocyanate, EiTC, BCECF and DNA aptamers.

In an embodiment, the present disclosure includes a process for preparing a fluorescent nanosensor for extracellular ion concentration measurements, the process comprising:
- treating a nanoparticle with a silane reagent under conditions to provide a silica shell containing nanoparticle;
- treating the silica shell containing nanoparticle with a second silane reagent in the presence of a fluorophore under conditions to provide a fluorescent silica shell containing nanoparticle, wherein the fluorescent silica shell comprises the fluorophore dispersed therein;
- reacting the fluorescent silica shell containing nanoparticle with a first functionalized silane reagent having a first functionality, under conditions to provide a functionalized nanoparticle comprising a functionalized silica shell; and
- reacting the functionalized nanoparticle with a substrate functionalized with a second functionalized silane reagent, the second functionalized silane reagent comprising a second functionality complementary to the first functionality;
- wherein the functionalized nanoparticle undergoes a cycloaddition reaction with the functionalized substrate to provide the fluorescent nanosensor;
- wherein the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure includes a process for preparing a fluorescent nanosensor for extracellular ion concentration measurements, the process comprising:
- treating a nanoparticle with a silane reagent under conditions to provide a silica shell containing nanoparticle;
- treating the silica shell containing nanoparticle with a second silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the substrate includes microarrays, beads, optical fibres, glass, modified or functionalized glass, quartz, mica, Si, SiO$_2$, modified silicon, thermoplastic polymers, polyvinyl alcohol, cellulose, paper and TiO$_2$.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate;

wherein the cycloaddition reaction is selected from [4+2] cycloadditions and [3+2] cycloadditions.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the fluorophore is selected from Oregon Green™, SBFI, PBFI, Fura Red™, CoroNa™ Green, FluoZin™, Newport Green™, Calcium Green™, Fluo-3, Magnesium Green™, Calcium Orange™, Calcium Crimson™, ISO, SNARF™, SNARF™ derivatives, MQAE, Phen Green™, SPQ, fluorescein 5(6)-isothiocyanate, EiTC, BCECF and DNA aptamers.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure includes a process for preparing a fluorescent nanosensor for extracellular ion concentration measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a first functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor;

wherein the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$.

In an aspect of the present disclosure, the spacer reagent is selected from silane reagent, $SiO_2$, a metal oxide and polydopamine.

In an embodiment, the present disclosure includes a process for preparing a fluorescent nanosensor for extracellular pH measurements, the process comprising:

treating a nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an embodiment, the present disclosure includes a process for preparing a fluorescent nanosensor for extracellular pH measurements, the process comprising:

treating a nanoparticle with a silane reagent under conditions to provide a silica shell containing nanoparticle;

treating the silica shell containing nanoparticle with a second silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized fluorescent silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an embodiment, the present disclosure includes a process for preparing a fluorescent nanosensor for extracellular pH measurements, the process comprising:

treating a nanoparticle with a spacer reagent under conditions to provide a spacer shell containing nanoparticle;

treating the spacer shell containing nanoparticle with a silane reagent in the presence of a fluorophore under conditions to provide a fluorescent silica shell containing nanoparticle, wherein the fluorescent silica shell comprises the fluorophore dispersed therein;

reacting the fluorescent silica shell containing nanoparticle with a functionalized silane reagent having a first functionality, under conditions to provide a functionalized nanoparticle comprising a functionalized fluorescent silica shell; and reacting the functionalized nanoparticle with a substrate functionalized with a second functionalized silane reagent, the second functionalized silane reagent comprising a second functionality complementary to the first functionality;

wherein the functionalized nanoparticle undergoes a cycloaddition reaction with the functionalized substrate to provide the fluorescent nanosensor.

In an aspect of the present disclosure, the spacer reagent is selected from silane reagent, $SiO_2$, a metal oxide and polydopamine.

In an embodiment, the present disclosure includes a process for depositing a photoluminescent nanostructure on a substrate surface, the process comprising:
reacting the photoluminescent nanostructure with a functionalized silane reagent having a first functionality, under conditions to provide a functionalized photoluminescent nanostructure; and
reacting the functionalized photoluminescent nanostructure with a substrate functionalized with a second functionalized silane reagent, the second functionalized silane reagent comprising a second functionality complementary to the first functionality;
wherein the functionalized photoluminescent nanostructure undergoes a cycloaddition reaction with the functionalized substrate to provide a fluorescent nanosensor.

In an embodiment, the present disclosure includes a process for depositing a photoluminescent nanostructure on a substrate surface, the process comprising:
reacting the photoluminescent nanostructure with a functionalized silane reagent having a first functionality, under conditions to provide a functionalized photoluminescent nanostructure; and
reacting the functionalized photoluminescent nanostructure with a substrate functionalized with a second functionalized silane reagent, the second functionalized silane reagent comprising a second functionality complementary to the first functionality;
wherein the functionalized photoluminescent nanostructure undergoes a cycloaddition reaction with the functionalized substrate to provide a fluorescent nanosensor;
wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

In an embodiment, the present disclosure includes a process for depositing a photoluminescent nanostructure on a substrate surface, the process comprising:
reacting the photoluminescent nanostructure with a functionalized silane reagent having a first functionality, under conditions to provide a functionalized photoluminescent nanostructure; and
reacting the functionalized photoluminescent nanostructure with a substrate functionalized with a second functionalized silane reagent, the second functionalized silane reagent comprising a second functionality complementary to the first functionality;
wherein the functionalized photoluminescent nanostructure undergoes a cycloaddition reaction with the functionalized substrate to provide a fluorescent nanosensor;
wherein the photoluminescent nanostructure further comprising a spacer shell interposed between a metallic core and a fluorescent silica shell.

In an embodiment, the present disclosure includes a process for depositing a photoluminescent nanostructure on a substrate surface, the process comprising:
reacting the photoluminescent nanostructure with a functionalized silane reagent having a first functionality, under conditions to provide a functionalized photoluminescent nanostructure; and
reacting the functionalized photoluminescent nanostructure with a substrate functionalized with a second functionalized silane reagent, the second functionalized silane reagent comprising a second functionality complementary to the first functionality;
wherein the functionalized photoluminescent nanostructure undergoes a cycloaddition reaction with the functionalized substrate to provide a fluorescent nanosensor;
wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate;
wherein the photoluminescent nanostructure further comprising a spacer shell interposed between a metallic core and a fluorescent silica shell.

In an embodiment, the present disclosure includes a fluorescent nanosensor for multiplex extracellular ion concentration measurements, the fluorescent nanosensor comprising at least two distinct photoluminescent nanostructures disposed on a substrate surface, wherein each of the distinct photoluminescent nanostructures emits a fluorescence emission in response to an extracellular ion concentration.

In an embodiment, the present disclosure includes a fluorescent nanosensor for multiplex extracellular ion concentration measurements, the fluorescent nanosensor comprising at least two distinct photoluminescent nanostructures disposed on a substrate surface, wherein each of the distinct photoluminescent nanostructures emits a fluorescence emission in response to an extracellular ion concentration; wherein the photoluminescent nanostructures comprise a fluorescent metallic core-silica shell containing nanoparticle, wherein the fluorescent silica shell comprises a fluorophore dispersed therein.

In an embodiment, the present disclosure includes a fluorescent nanosensor for multiplex extracellular ion concentration measurements, the fluorescent nanosensor comprising at least two distinct photoluminescent nanostructures disposed on a substrate surface, wherein each of the distinct photoluminescent nanostructures emits a fluorescence emission in response to an extracellular ion concentration; wherein the photoluminescent nanostructures comprise a fluorescent metallic core-silica shell containing nanoparticle comprising a spacer shell interposed between the metallic core and the fluorescent silica shell, and wherein the fluorescent silica shell comprises a fluorophore dispersed therein.

In an embodiment, the present disclosure relates to the use of a fluorescent nanosensor in accordance with the present disclosure for measuring a cellular activity, wherein the cellular activity is measured by determining changes in the concentrations of an ion selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

In an embodiment, the present disclosure relates to a method of detecting an extracellular ion concentration in a cell of a subject, the method comprising:

contacting a fluorescent nanosensor of the present disclosure with the cells; and measuring a fluorescence emission in function of the concentration of the ion concentration in the cells.

The foregoing and other advantages and features of the present disclosure will become more apparent upon reading of the following non-restrictive description of illustrative embodiments thereof, given by way of example only with reference to the accompanying drawings/figures.

BRIEF DESCRIPTION OF THE DRAWINGS/FIGURES

In the appended drawings/figures:

FIG. 1 illustrates the fluorescence intensity for Ag@SiO$_2$-FiTC core-shell particles grafted on a surface (blue) and dissolved cores (red) in accordance with an embodiment of the present disclosure. The enhancement factor was calculated by ratiometry of intensities at both maxima.

FIG. 2a is an epifluorescence microscopy photograph of an Ag@SiO$_2$-FiTC grafted-surface obtained using sodium ascorbate (left, exposition=50 ms) and ascorbic acid (right, exposition=25 ms) as reducing agents for the CuSO$_4$ in accordance with an embodiment of the present disclosure. Scale bars represent 200 μm. FIG. 2b is a Scanning Electron Microscope (SEM) image of a typical coverslip obtained using ascorbic acid as co-catalyzer in accordance with an embodiment of the present disclosure.

Figure 6:
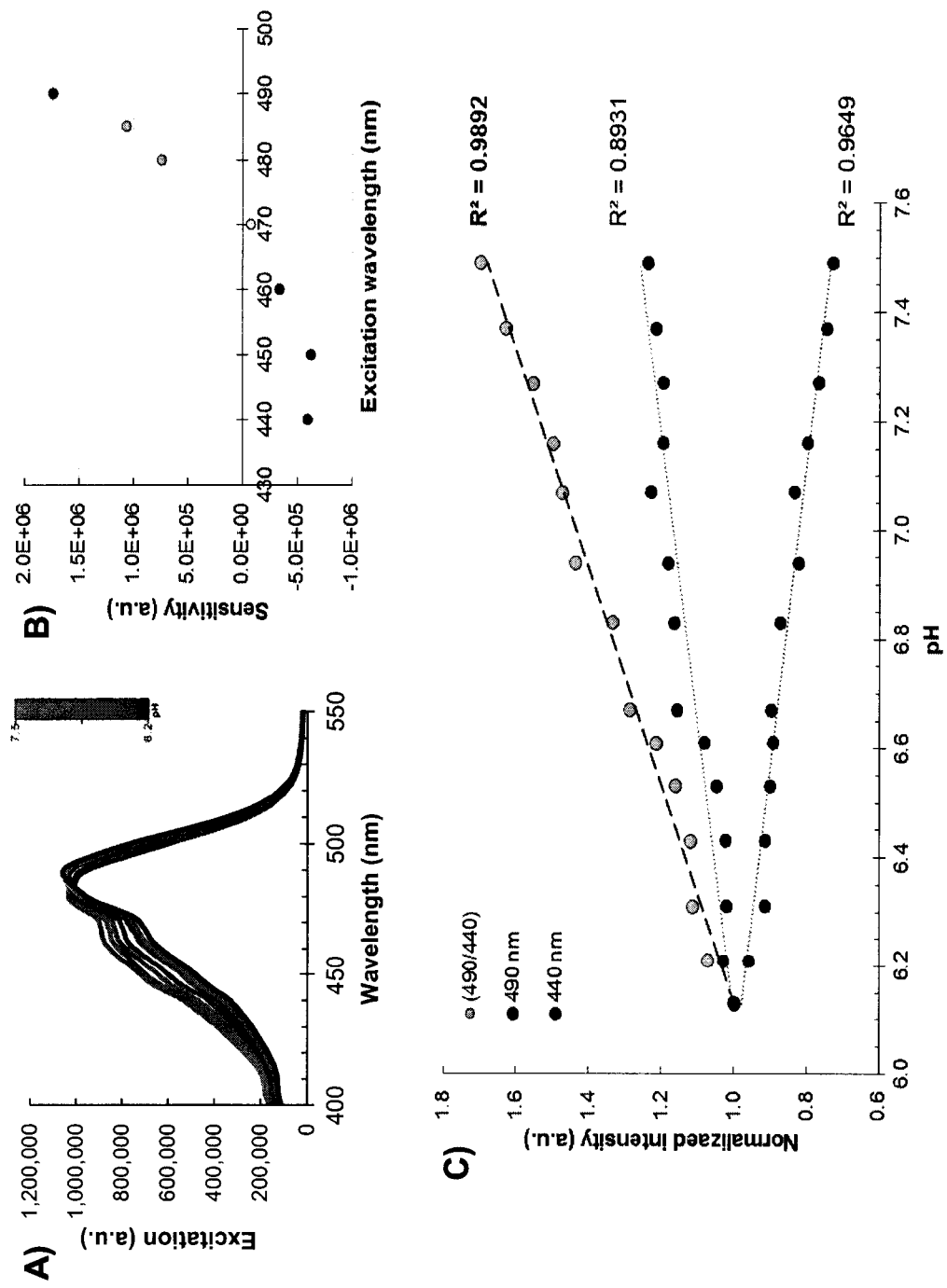

FIG. 6 is an illustration of the excitation spectra of Ag@SiO$_2$-FiTC with pH variations ($\lambda_{em}$=576 nm) (A); the sensitivity of the nanosensors in function of pH following different excitation wavelengths (B); and the emission and excitation maxima for 490 nm (blue) and 440 nm (red) respectively, as well as the calculated ratiometric values (green) (C) in accordance with an embodiment of the present disclosure.

Figure 7:
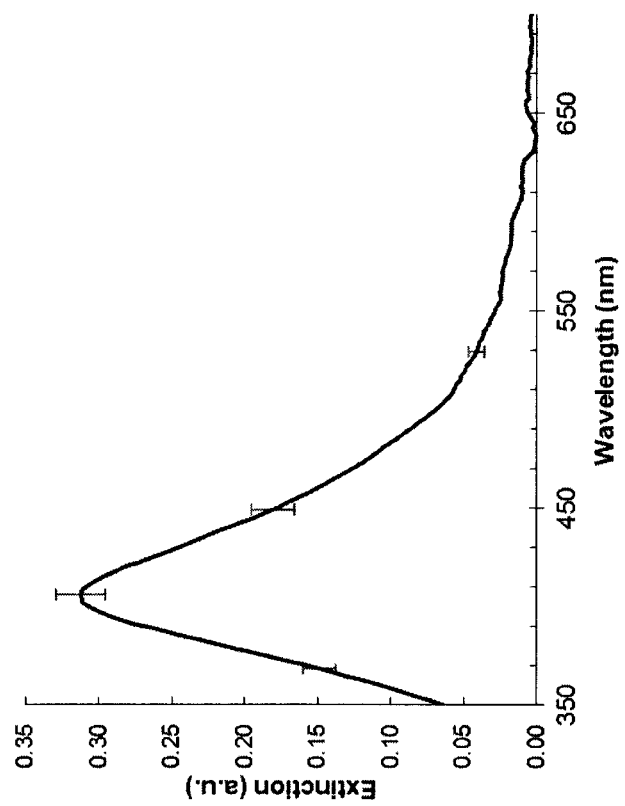

FIG. 7 is an illustration of the averaged extinction of Ag@SiO$_2$ particles grafted on microscope coverslips (n=3) in accordance with an embodiment of the present disclosure.

Figure 8:
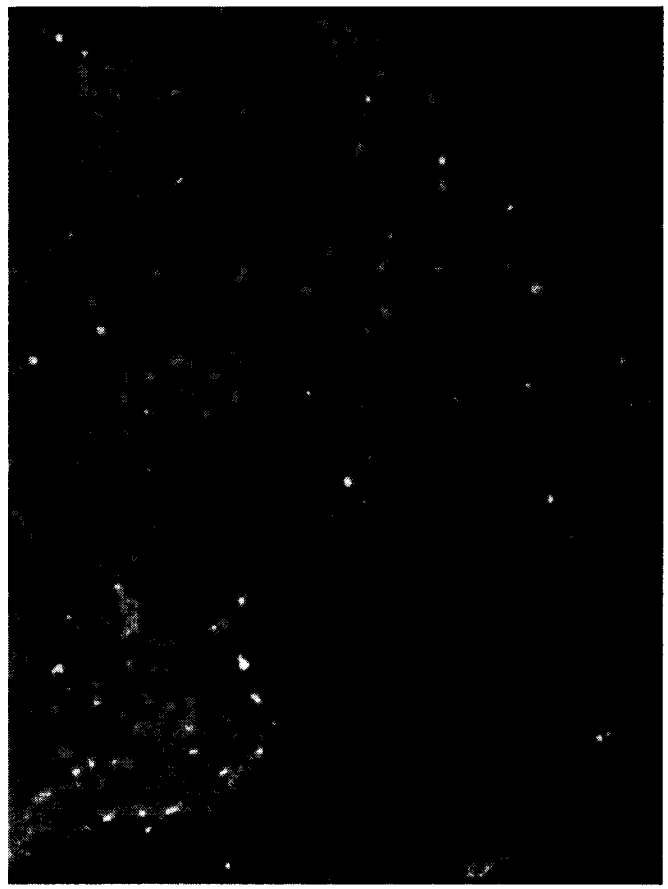

FIG. 8 illustrates an epifluorescence micrograph showing fluorescent surfaces (FiTC) and the cell nucleus (DAPI) using a 40× objective in accordance with an embodiment of the present disclosure.

Figure 9:
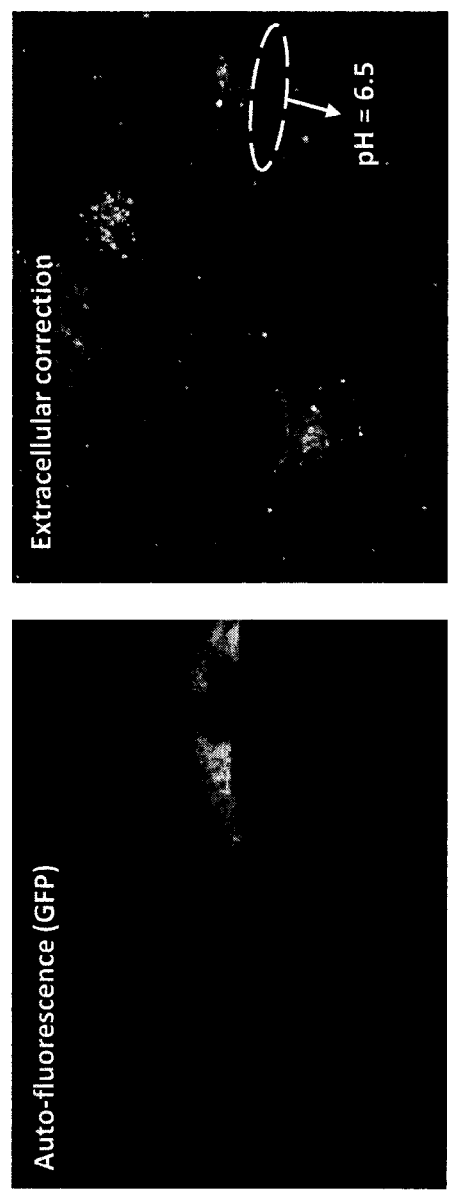

FIG. 9 illustrates epifluorescence micrographs for autofluorescence of cells (GFP) and ratiometric correction for extracellular pH in accordance with an embodiment of the present disclosure.

Figure 10:
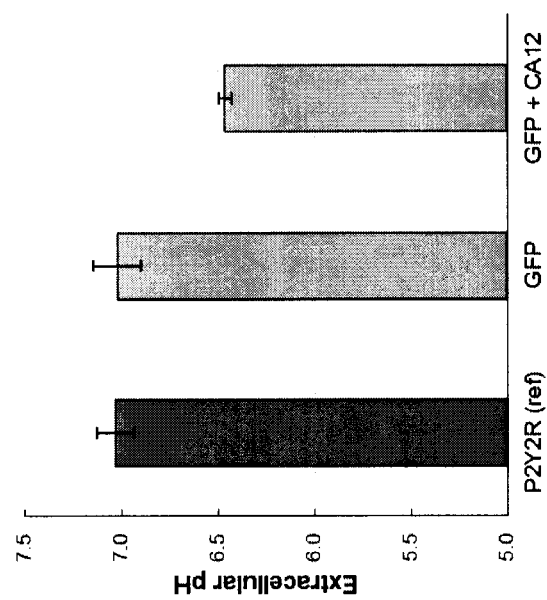

FIG. 10 is a graph illustrating various extracellular pH values for cells transfected with different plasmids in accordance with an embodiment of the present disclosure.

Figure 11:
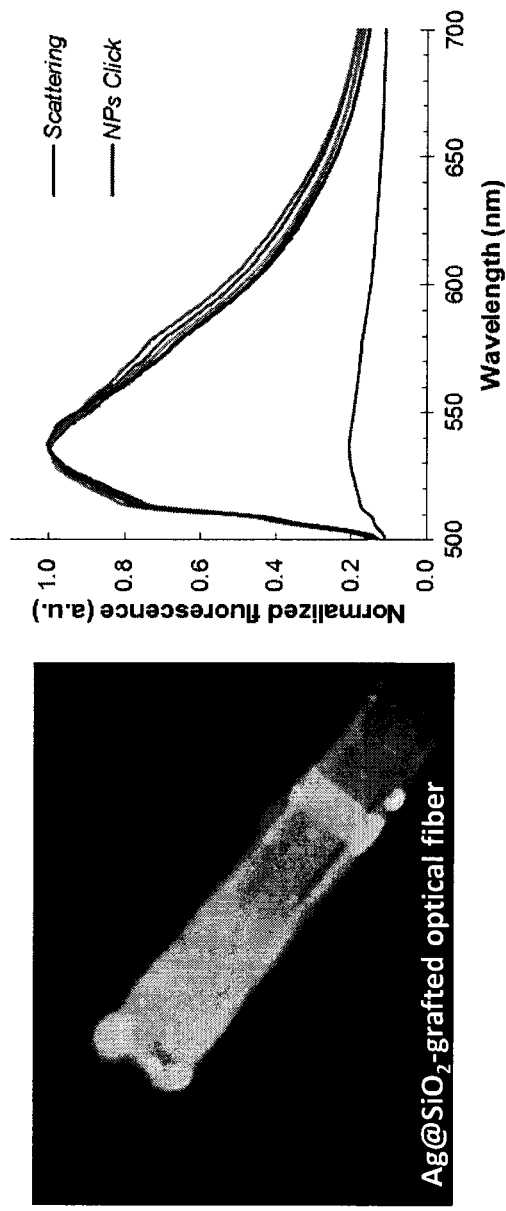

FIG. 11 illustrates an epifluorescence microscopy photograph of an Ag@SiO$_2$-FiTC grafted 3-D surface (optical fiber) and an associated fluorescence emission spectrum (n=5) in accordance with an embodiment of the present disclosure.

Figure 12:
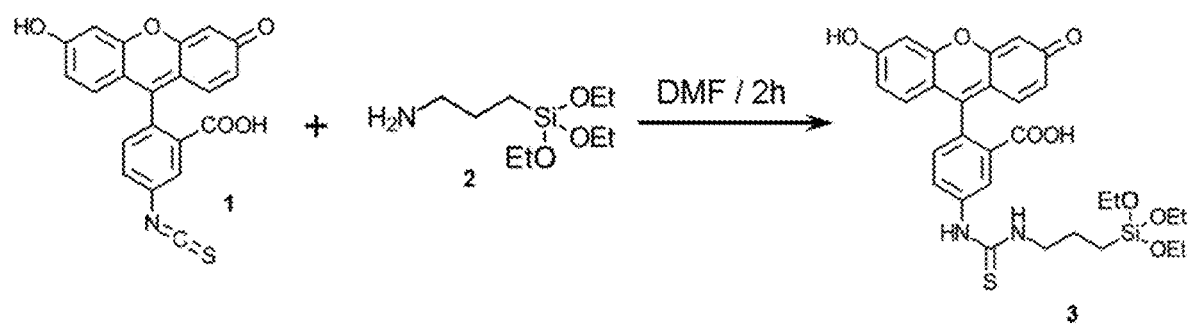
Figure 13:
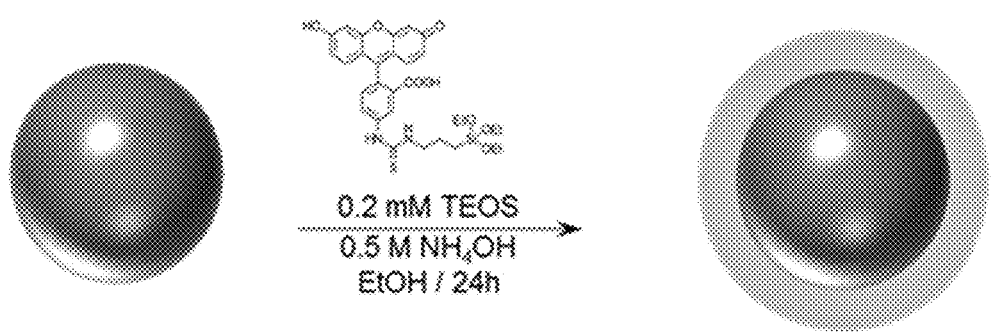

FIGS. 12-13 An embodiment of a silver core-silica shell containing fluorescent nanoparticle prepared in one embodiment of the present invention.

Figure 14:
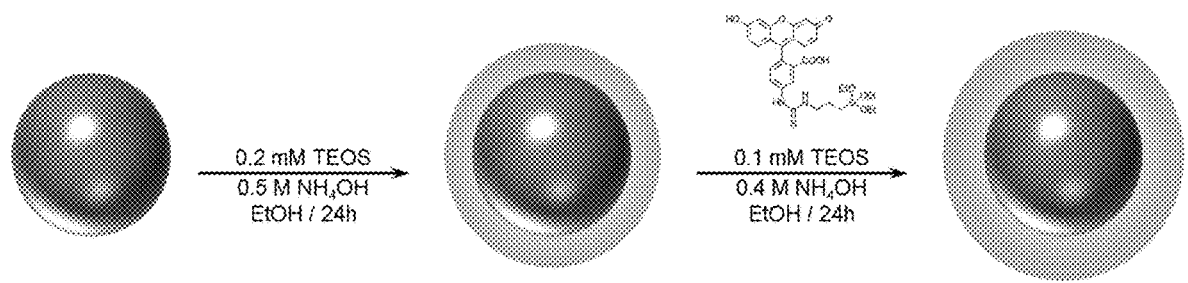

FIG. 14 An embodiment of a silver core-silica shell containing fluorescent nanoparticle of the present invention comprising a spacer shell or layer prepared in one embodiment of the present invention.

Figure 15:
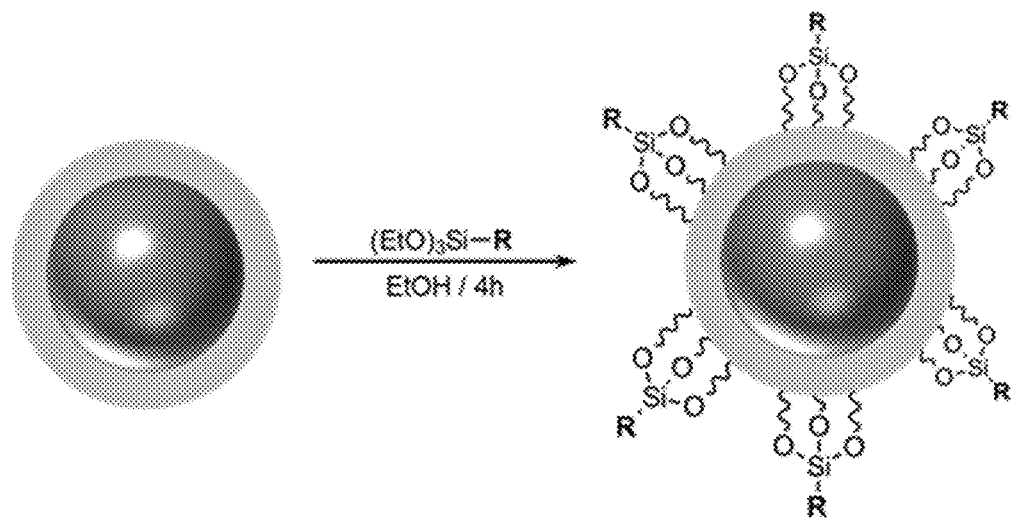

FIG. 15 An embodiment of a silver core-silica shell containing fluorescent nanoparticle of the present invention having a complementary silane-based functionality.

Figure 16:
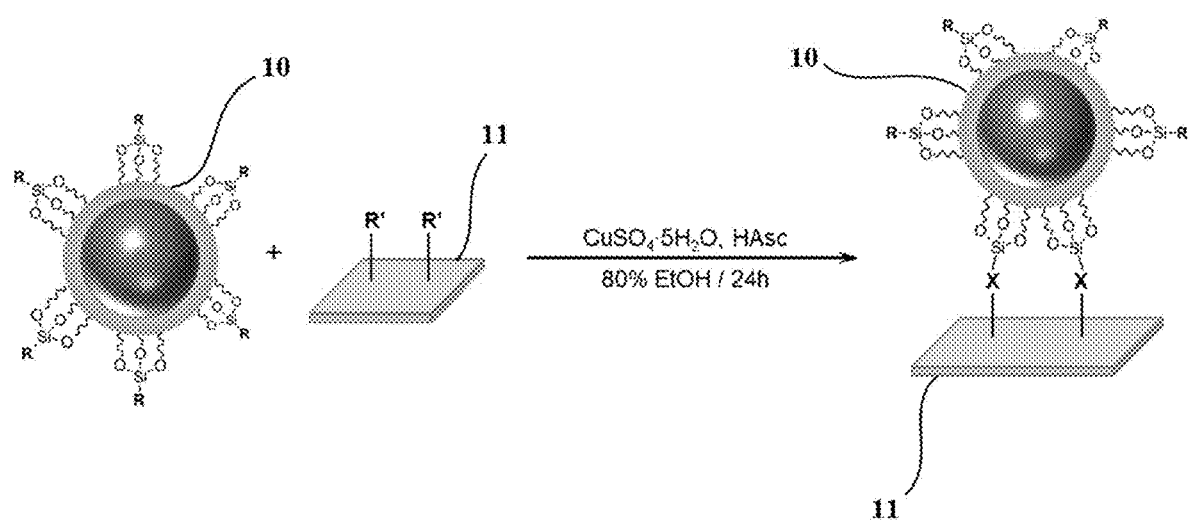

FIG. 16 An embodiment of a silver core-silica shell fluorescent nanoparticle of the present invention grafted onto a substrate surface.

DETAILED DESCRIPTION

Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this specification pertains.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material to product is maximized. Conversion may be maximized when greater than about 5, 10, 15, 20, 25, 30, 35, 40, 45, 50, 55, 60, 65, 70, 75, 80, 85, 90, 95 or 99% of the starting material is converted to product.

As used herein, the term "nanoparticle" refers to a particle having a dimension of less than 1 micron (1 μm) and may include nanoparticles formed from a single material or formed from a combination of materials. In an embodiment, the nanoparticle comprises a metal core and a silica shell. In an embodiment, the nanoparticle comprises a metal core and a silica shell in which is embedded a fluorophore. In an embodiment, the particle has a size of less than 800 nanometers (800 nm) such as less than 500 nanometers (500 nm) and further such as less than 100 nanometers (100 nm). In a further embodiment, the nanoparticles have an average particle size generally ranging from 1 nm to less than 1000 nm, such as from 10 nm to 500 nm and further such as from 30 nm to 100 nm.

As used herein, the term "alkyl" refers to straight-chain or branched-chain alkyl residues. This also applies if they carry substituents or occur as substituents on other residues, for example in alkoxy residues, alkoxycarbonyl residues or arylalkyl residues. Substituted alkyl residues are substituted in any suitable position. Examples of alkyl residues containing from 1 to 10 carbon atoms are methyl, ethyl, propyl, butyl, pentyl, hexyl, heptyl, octyl, nonyl and decyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "metal" or "metallic" means a metal in elemental form or an alloy having typical metallic properties such as electrical conductivity.

As used herein, the term "spacer" means a shell or shell layer interposed between a metallic core and a fluorescent shell, as an alternative to the fluorescent shell directly covering or being directed deposited over the metallic core.

The terms "dispersed" and "dispersion", as used herein, refer to the distribution of a fluorophore, substantially uniformly throughout a silica shell.

The term silane as used herein is represented by the formula $SiA^1A^2A^3A^4$ where $A^1$, $A^2$, $A^3$ and $A^4$ can be, independently, hydrogen, or a substituted or unsubstituted alkyl, alkoxy, alkenyl, alkynyl, aryl, heteroaryl or cycloalkyl. The term functionalized silane reagent is represented by the formula $R-SiA^1A^2A^3$, wherein R is a group comprising a functionality capable of participating in a cycloaddition reaction.

Preparation of Fluorescent Nanoparticles

Quantitative extracellular measurements are not widely used for biomedical studies. Because of their hydrophobicity, a majority of organic fluorophores can diffuse through the phospholipid bilayer and thus emit cytosolic-characteristic fluorescence. Similar properties are also known for silica nanoparticles. In an embodiment, the present disclosure relates to a grafting method for confining an ionic sensor to the extracellular domain. In an embodiment, the present disclosure relates to a chemical grafting method for confining an ionic sensor to the extracellular domain. In a further embodiment of the present disclosure, the ionic sensor is a fluorescent nanosensor. In yet a further embodiment of the present disclosure, the ionic sensor is a metallic core-silica shell fluorescent nanoparticle. In yet a further embodiment of the present disclosure, the ionic sensor is a silver core-silica shell fluorescent nanoparticle (Ag@SiO$_2$-FiTC). In yet a further embodiment of the present disclosure, the ionic sensor is attached to a substrate providing a functionalized substrate suitable for in vitro studies. In yet a further embodiment of the present disclosure, the functionalized substrate is directly implanted in the culture medium. In yet a further embodiment of the present disclosure, the substrate may be a 2-D substrate of a 3-D substrate, a non-limiting example of which includes an optical fiber.

In a general way, the functionalized substrates can be prepared using click chemistry in accordance with general methods described in the literature or using the methods described herein. In an embodiment of the present disclosure, click chemistry yields stable chemical binding between the fluorescent nanoparticle and a substrate. In a further embodiment of the present disclosure, click chemistry allows for the grafting of a maximal number of the fluorescent nanoparticles on a substrate. In a further embodiment of the present disclosure, a "click" reaction is used to graft metallic core-silica shell containing fluorescent nanoparticles (metal@SiO$_2$ NPs) on a silica surface functionalized with complementary functionalities (silanes comprising a complementary functionality). In a further embodiment, stable chemical binding between the fluorescent nanoparticles and a complementarily functionalized substrate nullifies the cytosolic signal and metabolic invasiveness (i.e. endocytosis of the fluorescent nanoparticle by a biological cell).

In an embodiment of the present disclosure, complementary functionalities undergo a cycloaddition reaction resulting in the grafting of fluorescent nanoparticles on a substrate. Non-limiting examples of cycloaddition reactions include [4+2] cycloadditions and [3+2] cycloadditions.

In a further embodiment of the present disclosure, silver core-silica shell fluorescent nanoparticles (Ag@SiO$_2$ NPs) are grafted on a silica surface. In yet a further embodiment of the present disclosure, silver core-silica shell fluorescent nanoparticles are grafted on a silica surface to prepare proton-sensitive devices. In yet a further embodiment of the present disclosure, silver core-silica shell fluorescent nanoparticles (Ag@SiO$_2$ NPs) are grafted on an optical fiber.

In an embodiment of the present disclosure, a silver core-silica shell containing fluorescent nanoparticle (Ag@SiO$_2$ NP) is prepared as illustrated in FIG. 12 and FIG. 13. Reaction of fluorescein 5(6)-isothiocyanate (1) with 3-aminopropyl)triethoxysilane (2) provided fluorescent compound 3 (FIG. 12). Silver nanoparticles were subsequently reacted with TEOS in the presence of 3 resulting in the formation of a silica shell layer on the silver nanoparticles in which 3 is dispersed. The silica layer is fluorescent due to the dispersion of 3 throughout the silica layer (FIG. 13). Moreover, the subsequent grafting efficiency is improved due to the fluorophore being dispersed in the silica layer thus leaving the surface of the silica layer more accessible for subsequent functionalization and cycloaddition.

In an embodiment of the present disclosure, a silver core-silica shell containing fluorescent nanoparticle (Ag@SiO$_2$ NP) further comprising a spacer shell or layer is prepared as illustrated in (FIG. 14). Condensation of a spacer layer or spacer shell directly on the metallic core is achieved without the fluorescent precursor. Non-limiting examples of such spacer layers include silica, polydopamine, and metal oxides. In an embodiment of the present disclosure, this spacer layer not only functions as a low porosity protective coating for the plasmonic metal core, but also as a controlled spacer for more specific positioning of the fluorophores in the local electric field. Variations in the thickness of the spacer layer can thus be used to optimize the fluorescence of the fluorophores dispersed in the subsequently deposited fluorescent layer.

The silver core-silica shell containing fluorescent nanoparticles (Ag@SiO$_2$ NPs) are subsequently grafted on a substrate surface. Non-limiting examples of substrate surfaces include silica surfaces. Further non-limiting examples of substrate surfaces include surfaces comprising reactive hydroxide functions such as TiO$_2$, polyvinyl alcohol or cellulose surfaces. In an embodiment of the present disclosure, the silver core-silica shell containing fluorescent nanoparticles (Ag@SiO$_2$ NPs) are reacted with a functionalized silane reagent in a suitable solvent and over a period of time sufficient to functionalize the silver core-silica shell fluorescent nanoparticles with one of the complementary silane-based functionalities (FIG. 15). In an embodiment of the present disclosure, the functionalized silane reagent comprises the general formula (R$^1$O)$_3$Si—R, wherein R$^1$ is an alkyl group and R is a group comprising a functionality capable of participating in a cycloaddition reaction. In a further embodiment of the present disclosure, the functionalized silane reagent comprises the general formula (EtO)$_3$Si—R, wherein R is a group comprising a functionality capable of participating in a cycloaddition reaction. Non-limiting examples of solvents include polar protic solvents such as ethanol. Moreover, typical reaction times range from about 1 hour to about 10 hours. In an embodiment of the present disclosure, the reaction time was 4 hours. The functionalized silane reagent reacts with the silica layer of the silver core-silica shell containing fluorescent nanoparticles and is covalent attached thereto. In an embodiment of the present disclosure, the solvent is ethanol. Non-limiting examples of (EtO)$_3$Si—R are illustrated in FIG. 15.

As illustrated in FIG. 16, the silver core-silica shell fluorescent nanoparticles (10) are subsequently grafted on a substrate (11) surface functionalized with a functionality R' capable of undergoing a cycloaddition reaction with the latent R group of the silver core-silica shell fluorescent nanoparticles.

In an embodiment of the present disclosure, the substrate surface is a silica surface. In an embodiment of the present disclosure, the substrate surface is functionalized using a functionalized silane reagent comprises the general formula (R$^1$O)$_3$Si—R', wherein R$^1$ is an alkyl group and R' is a group comprising a functionality capable of participating in a cycloaddition reaction. In a further embodiment of the present disclosure, the functionalized silane reagent comprises the general formula (EtO)$_3$Si—R', wherein R' is a group comprising a functionality capable of participating in a cycloaddition reaction. Non-limiting examples of (EtO)$_3$Si—R' include:

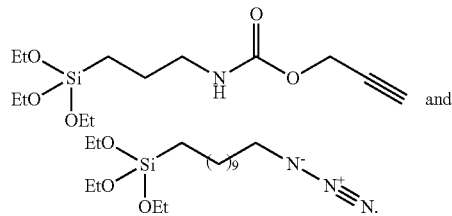

In an embodiment of the present disclosure, the grafting of silver core-silica shell fluorescent nanoparticles onto a substrate surface results in a proton-sensitive device. The silver core-silica shell fluorescent nanoparticle-coated silica surface provides a fluorescent analytical surface for measuring pH values. The response of the analytical surface to different pH values was measured through fluorescence microfluidic experiments in different buffers. In an embodiment of the present disclosure, the proton sensitive devices are used to quantify the extracellular pH for multiple live samples by fluorescence microscopy. In an embodiment of the present disclosure, the proton sensitive devices are used to quantify the extracellular pH for multiple live samples comprising a therapeutic agent by fluorescence microscopy, where the presence of the therapeutic agent leads to an increase in extracellular acidity.

The stability of a substrate-bound triazole ring formed by Huisgen cycloaddition of alkyne and azide functions is well known.[27,28] However, the use of this cycloaddition reaction for grafting nanoscopic materials on lamellar substrates has yet to be explored. In an embodiment of the present disclosure, the cycloaddition reaction for grafting a metallic core-silica shell comprising fluorescent nanoparticle onto a functionalized substrate is catalyzed using a catalyst such as copper sulfate (CuSO$_4$). In order to increase the solubility of the copper sulfate catalyst in ethanol, ascorbic acid was used to generate Cu(I) in situ; this oxidized copper species is used to activate the terminal alkyne.[29, 30] A person skilled in the art would appreciate that the cycloaddition reaction could be performed using other catalysts capable of activating a terminal alkyne. Non-limiting examples of such catalysts include CuSO$_4$·5H$_2$O/Cu$_{(s)}$, Cu(OAc)$_2$/Ascorbate, Cu(MeCN$_4$)PF$_6$, CuBr, CuI, CuOTf(C$_6$H$_6$), Cu$_{(s)}$/NEt$_3$, Cu$_{(s)}$/CuSO$_4$/microwave, Ru-cp* (cp*=pentamethylcyclopentadiene), Ni$^{2+}$, Pd$^{2+}$ and Pt$^{2+}$. In yet a further embodiment, the cycloaddition reaction is performed using nitrile and azide functions. In yet a further embodiment, the cycloaddition reaction is performed using nitrile oxides and alkynes. In yet a further embodiment, the cycloaddition is performed using alkene and diene functions. Non-limiting examples of various R and R' group functionalities, as well as the resulting cycloadduct, are illustrated in Table 1.

Figure 3:
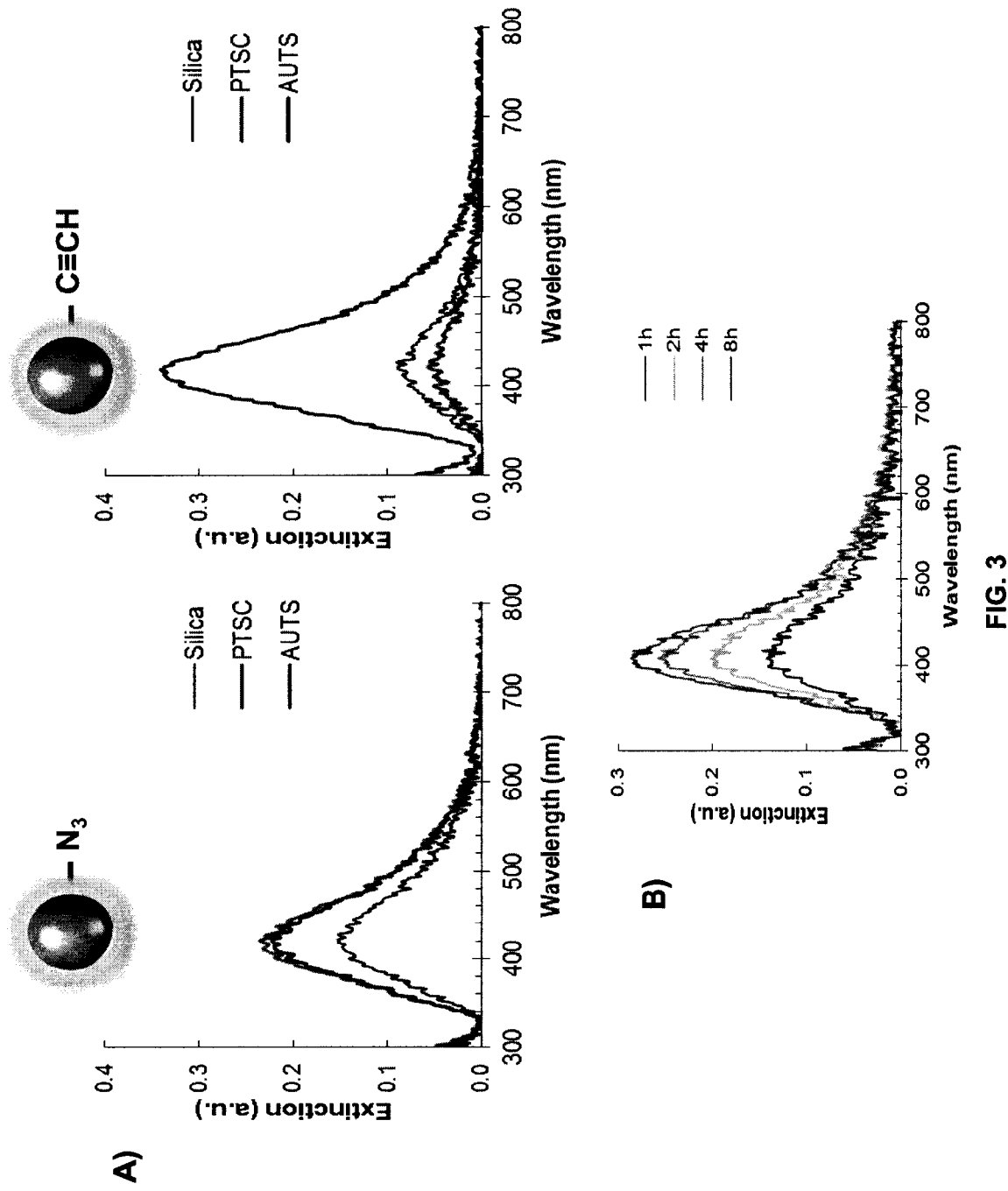
FIG. 3 is an illustration of the plasmonic extinction of Ag cores for Ag@SiO$_2$-grafted surfaces with different functionalities in accordance with an embodiment of the present disclosure: A) relative functionalization; B) click reaction time.
Figure 4:
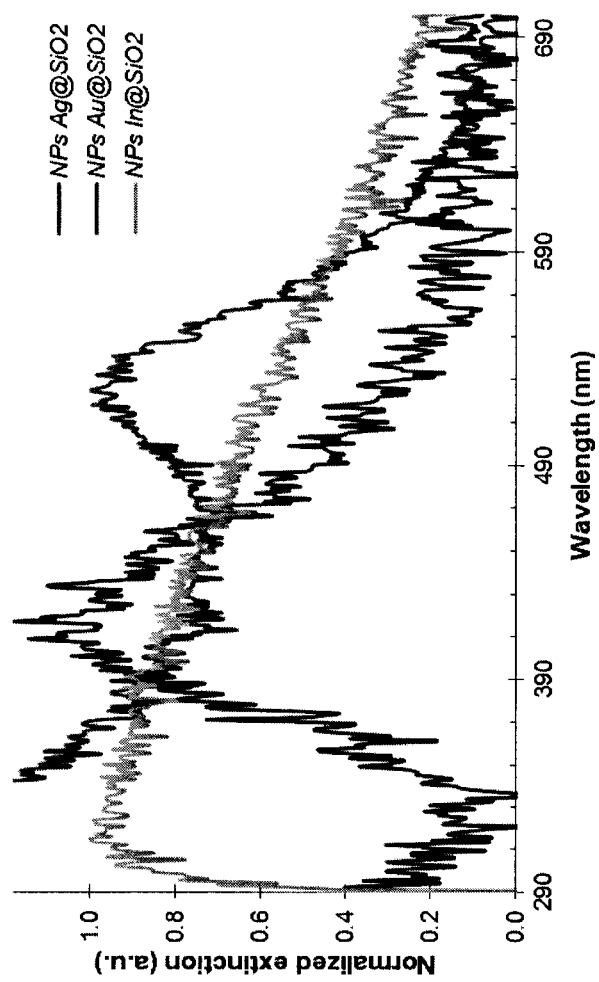
FIG. 4 is an illustration of the plasmonic extinction of different types of core-shell nanoparticles on silica coverslips in accordance with an embodiment of the present disclosure.

Prior to functionalization with a suitable reagent for subsequent "click" reaction (cycloaddition reaction) with the functionalized core-silica shell fluorescent nanoparticles, the substrate surface is subjected to a treatment using a Piranha solution. The presence of plasmonic extinction on surfaces with non-complementary functional groups is indicative that robust surface treatment (i.e. activation by the Piranha solution) can induce electrostatic attraction of the nanoparticles to the substrate surface. In an embodiment of the present disclosure, this proximity results in the covalent binding of the copper-activated alkyne at the nanoparticle surface with the azide functionalized silica slide. In comparison, modification of the silica shell by covalent attachment of AUTS appears to display much less chemical fixation and more non-covalent electrostatic interaction between the modified surfaces. These optimized parameters for the "click" reaction of nanoparticles on lamellar substrates show homogeneous fixation increasing with duration in contact time (FIG. 3). Since the functionalization and grafting processes use the reactivity of the outer surface of the core-shell nanoparticles, only the concentration of the suspensions and the available surface area influence the reaction for other nanoparticular systems. Along with commercial Ludox™ silica particles, silver, gold and indium cores comprising a silica shells were grafted homogeneously on lamellar surfaces (FIG. 4).

Spectroscopic pH Measurement with $Ag@SiO_2$-FiTC Surfaces

Because of the chemical stability of the covalent binding between the core-silica shell fluorescent nanoparticles and the substrate surface, a lamellar surface comprising fluidic molecules has been prepared that can be contacted with various analytical solutions. The use of core-shell particles in these lamellar systems provides multiple advantages, notably the high surface area in contact with the analytical solutions and the capability for small cations to diffuse through the silica shell to modify the local environment of the sensitive fluorophores dispersed therein. In an embodiment of the present disclosure, the lamellar systems are used for spectrofluorimetry analysis of flowing solutions. In an embodiment of the present disclosure, the fluorophore is fluorescein, a compound well-known for its variable quantum yields with varying pH values, leading to a linear increase in fluorescence emission in a physiological pH range—from 5 to 8 approximately.[31] In a further embodiment of the present disclosure, other fluorophores, non-limiting examples of which include SNARF (seminaphthorhodafluor) derivatives, are used to produce core-silica shell containing fluorescent nanoparticles. These nanoparticles are also suitable for use in the lamellar systems of the present disclosure for transducing varying pH values into fluorescence emissions.[32]

Figure 5:
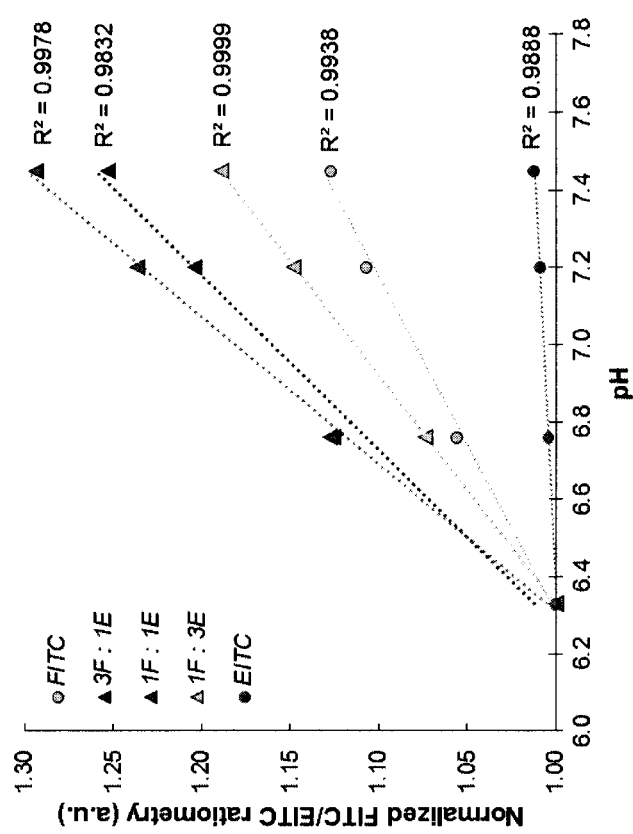
FIG. 5 is an illustration of the linearity of the ratiometric signal obtained with silica surfaces covered with Ag@SiO$_2$-FiTC and Ag@SiO$_2$-EiTC in different proportions in accordance with an embodiment of the present disclosure. Fluorescence emission spectra were measured with synchronous scanning of excitation with and offset of 20 nm.

In an embodiment of the present disclosure, core-silica shell containing fluorescent nanoparticles comprising eosin isothiocyanate (EiTC) were co-grafted onto microscopy coverslips with core-silica shell containing fluorescent nanoparticles comprising FiTC. The resulting fluorescence emission spectra illustrate that it is possible to distinguish between differing fluorescent ionophores (FIG. 5). Moreover, these results illustrate that it is possible to apply a similar ratiometry for multiplex detection in complex samples, without unpredictable FRET energy transfers. Moreover, since the fluorescence emission spectrum of EiTC is less affected by protonation changes, a ratiometry between the variation in emission of FiTC at 512 nm and EiTC at 543 nm was possible. Moreover, the positive and weak variability in EiTC emission with pH confirms the stability of the covalent grafting of $Ag@SiO_2$ nanoparticles following the method of the present disclosure. With synchronous scanning of excitation and emission wavelengths and an offset of 20 nm, consistent with the Stokes shift of fluorescein, the calculated slopes increase in a linear manner—with the exception of 3 FiTC:1 EiTC, where the overlap between both bands creates no significant shoulder around 540 nm.

Depending on its different anionic or cationic forms, the excitation spectra of FiTC as a function of pH show a distinct shoulder or inflection point at 470 nm, indicative of a change in the sensitivity of the fluorophore (FIG. 6a). The fluorophore becomes relatively stable to changes in pH at about 470 nm. As can be observed in FIG. 6b, the slope reaches a maximal value at about 490 nm and minimal values at about 440 and 450 nm. Because of the increased linearity of the slopes for emission intensities measured at 512 nm and an excitation wavelength of 440 nm, a ratiometry with 490 nm was used for normalization purposes. The calculated values presented in FIG. 6c are illustrative of the detection sensitivity achieved using the present method. Moreover, the linearity can be enhanced by the attenuation of experimental artefacts present in both values for excitation at 490 and 440 nm. This normalization method proves to be effective for comparing fluorescence intensity changes between different substrates (FIG. 7).

Extracellular pH Measurements with Functionalized Surfaces

Ratiometric fluorophores are well-known to be particularly efficient in fluorescence microscopy analysis techniques, where different filters can be used for selecting appropriate excitation wavelengths.[33,34] Since this normalization can be used to compare ratiometric intensities between different surfaces, their application for extracellular pH measurements provides a useful tool in multiple biomedical studies. In an embodiment of the present disclosure, human cardiac fibroblasts were studied because of their attractive adhesive properties on surfaces in culture mediums, thus inducing a close proximity between the cellular membrane and the functionalized surfaces of the present disclosure. Protection of the plasmonic silver cores with the dye-doped silica shell (dye or fluorophore dispersed in the silica layer) is enough to minimize leeching of $Ag^+$ ions—a known cytotoxic species.[35,36] The cells adhered nicely everywhere on the functionalized substrates (FIG. 8). In a further embodiment of the present disclosure, various adhesive eukaryote cells or bacterial organisms were studied using the functionalized surfaces of the present disclosure. In yet a further embodiment of the present disclosure, lung, cardiac, neuronal, and stomach cells as well as associated tissues were studied using the functionalized surfaces of the present disclosure.

Calibration values were measured by changing the acidity of the culture buffer with additions of nitric acid. By using two different excitation filters—483 to 495 nm and 431 to 441 nm—which correspond approximately to those used in the spectroscopic measurements, the resulting calibration ratiometry was linear. The study in cells transfected with plasmids incorporating genes for green fluorescent protein (GFP) and the over-expression of different membrane proteins was achieved with promising results. Since the emission wavelengths of GFP overlap with those of FiTC, cellular auto-fluorescence regions were subtracted from the final images (FIG. 9). Multiple regions of interest were selected near cell membranes in different micrographs and the ratiometric values were converted into extracellular pH. Instrumental errors were observed to increase with the presence of intracellular GFP. Moreover, increased membrane activity with the enhanced expression of AC12 proteins (carbonic anhydrase) leads to noticeable acidification of the medium (FIG. 10). The calculated values were verified and confirmed by conventional cytometry analysis with BCECF.

The fluorescence lifetime is notably shorter than biological mechanisms, thus allowing a higher temporal resolution in biomedical studies. Moreover, plasmonic enhancement of fluorescence in core-shell nanoparticles imparts the silica monolayer with increased luminescence intensity and resistance to photobleaching, thus allowing prolonged analysis of various cellular mechanisms, notably cellular division, resistance to therapeutic agents and intercellular signalling (i.e. cellular activity that can translate into measurable pH variations). The fluorescent Ag@SiO$_2$-grafted coverslips of the present disclosure can be easily handled and the image processing ratiometry is easily transposable on any commercial epifluorescence microscope equipped with a camera and basic software.

Preparation of a Fluorescent Optical Fiber using Functionalized Ag@SiO$_2$-FiTC Nanoparticles.

In an embodiment, the core-silica shell containing fluorescent nanoparticles of the present disclosure are grafted on a 3-D surface such as an optical fiber. In an embodiment, silver core-silica shell containing fluorescent nanoparticles (Ag@SiO$_2$ NPs) are grafted onto the tip of an optical fiber (FIG. 11). Excitation at 488 nm, resulted in the emission of fluorescence that was subsequently transmitted through the fiber and measured at the opposite end of the optical fiber using a spectrophotometer. In a further embodiment of the present disclosure, an optical fiber, functionalized with silver core-silica shell containing fluorescent nanoparticles was used to quantify pH values both in-vivo and in-vitro. The fluorescent extremity of the optical fiber was contacted with a variable biological medium providing for direct measurements of localized pH variations.

Extracellular Measurements of Various Biological ions with Functionalized Surfaces Various ions can be measured using the fluorescent nanosensors of the present disclosure. Indeed, depending on the choice of fluorophore, the core-shell nanoparticles of the present disclosure show sensitivity to various ions or biomolecules. Non-limiting examples of biological ions include $Ca^{2+}$, $Zn^{2+}$, $Mg^{2+}$, $Na^+$, $K^+$, $Cl^-$ and ATP. Furthermore, non-limiting examples of various ions as well as the associated fluorophores are illustrated in Table 2. Non-limiting examples of biomolecules include adenosine triphosphate (ATP), dopamine, glutamate, serotonin and cyclic adenosine monophosphate (cAMP).

In a further embodiment of the present disclosure, the architecture of the fluorescent nanosensor is varied in other to maximize the analytical properties of the sensor. In an embodiment, the architecture is varied by modifying at least one of the plasmonic core composition, size and shape, shell composition and thickness.

Experimental

A number of examples are provided herein below illustrating the preparation of metallic core-silica shell containing fluorescent nanoparticles in accordance with various embodiments of the present disclosure. The following non-limiting examples are illustrative of the present disclosure.

Chemicals and reagents: Sodium citrate tribasic dihydrate (≥99.0% ACS grade), fluorescein 5(6)-isothiocyanate (FiTC; 90%), triethylamine (≥99.5%), (3-aminopropyl)triethoxysilane (APTES; ≥98%), ammonium hydroxide solution (28-30% NH$_3$), and L-ascorbic acid (HAsc; ≥99.0%) were purchased from Sigma-Aldrich. Silver nitrate (99.9995%) was obtained from Strem Chemicals, triethoxysilane (TEOS; 99.9%) from Alfa Aesar, and anhydrous N,N-dimethylformamide (DMF; 99.8%) from EMD Chemicals. O-(propargyloxy)-N-(triethoxysilylpropyl)-carbamate (PTSC; 90%) was purchased from Gelest, 11-azidoundecyl-trimethoxysilane (AUTS; ≥95%) from SiKÉMA and copper sulfate pentahydrate (≥98.5%) from VWR International. Buffers were prepared with potassium phosphate monobasic (≥99.0%, Anachemia), MES monohydrate (99.00%, VWR), or HEPES (99%, Fisher Scientific), and precise volumes of sodium hydroxide (97.0% ACS, BDH) aqueous solution. Unless otherwise specified, every chemical reagent was used without further purification. Ultrapure water (18.2 MΩ) was used in all experiments unless specified and anhydrous ethanol, obtained from Commercial Alcohols, was used as a solvent. All glassware for nanoparticles synthesis was conditioned with concentrated nitric acid, and then rinsed thoroughly with water.

Preparation of Silver Nanoparticles

The silver cores of the fluorescent nanoparticles of the present disclosure were prepared in accordance with known literature procedures following a scaled-up reduction methodology.[17,24,25] Accordingly, sodium citrate tribasic dihydrate (114 mg) was dissolved in water (500 mL, 0.77 mM) and heated to the boiling point under vigorous stirring. Afterward, silver nitrate (90 mg) in 500 µL of water is quickly added to the mixture, and kept at this temperature during 50 minutes before gradually cooling under moderate agitation. The total volume is adjusted to 350 mL with deionized water.

Preparation of Fluorescent Silica Shell (Ag@SiO$_2$-Fluorophore)

A fluorescent silane molecule was prepared using a fluorophore molecule following known literature procedures.[12,14,16,24] For example, FiTC (2.2 mg), a pH-sensitive fluorophore, was added to DMF (114 µL), triethylamine (1.6 µL) and APTES (1.6 µL) and left to agitate for 2 h yielding a 50 mM solution of the desired molecule (FiTC-APS). This mixture was then diluted to a volume of 13.5 mL with anhydrous ethanol.

Figure 1:
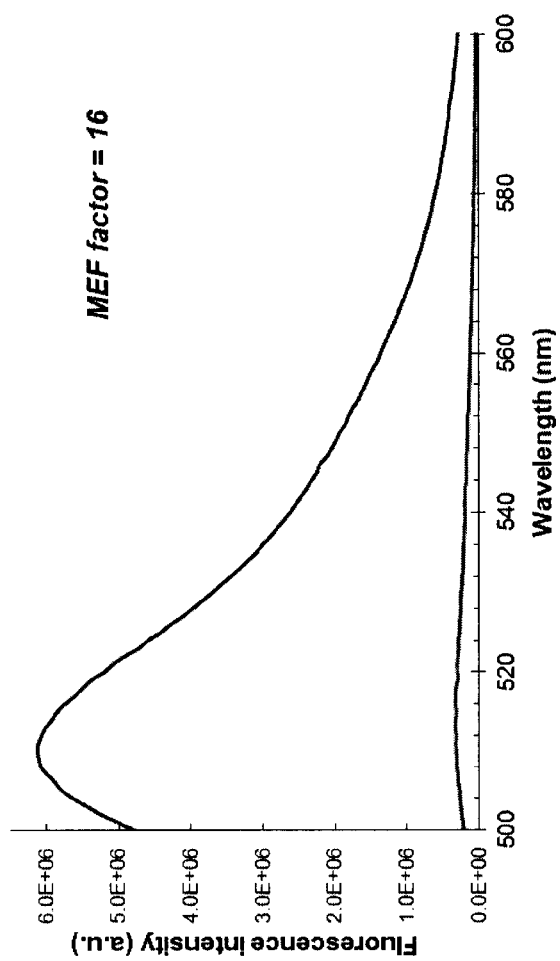
Figure 2:
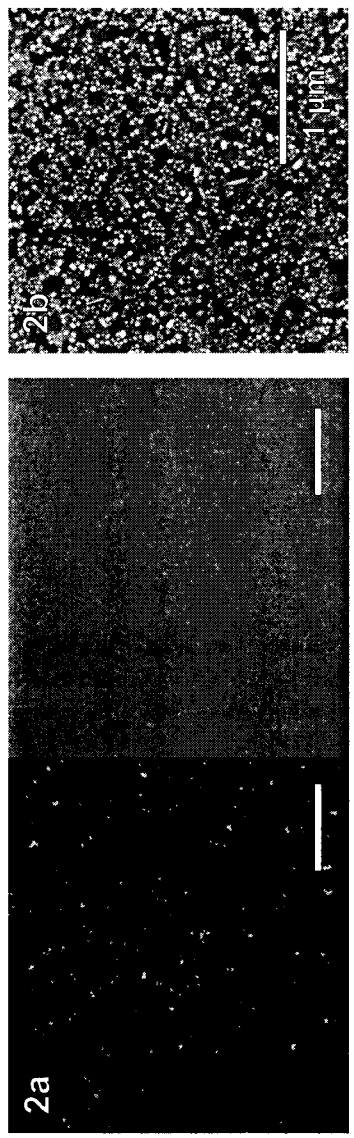

Condensation of a silica shell on the silver cores was achieved using experimental conditions adapted from Blaaderen et al.[26] A volume (100 mL) of the previously prepared suspension of Ag nanoparticles was diluted in ethanol (600 mL) followed by the addition of TEOS/EtOH (14 mL of 10 mM) and ammonium hydroxide (8 mL), resulting in the formation of silica coated Ag nanoparticles. In an embodiment of the present disclosure, the thickness of the resulting silica layer ranges from about 10 to about 20 nm. In a further embodiment of the present disclosure, the thickness of the resulting silica layer ranges from about 15 to about 20 nm. Shortly after the addition of TEOS/EtOH, FiTC-APS (4.4 mL) was added and the resulting reaction mixture was left to react over a period of 20-24 h at room temperature. In an embodiment of the present disclosure, the FiTC-APS was added about 15 minutes following the addition of the TEOS/EtOH reagent. The resulting suspension was subsequently centrifuged several times (11 000 RCF, 20 minutes). The fluorophore is dispersed in the silica layer near the plasmonic core of the resulting fluorescent nanoparticle while keeping the external surface of the silica layer free for further functionalization with additional reagents for grafting on a substrate. The influence of the plasmonic core on the fluorescence intensity was measured by dissolution of silver cores with dilute nitric acid (FIG. 1).

Click" Grafting of Metal@SiO$_2$ NPs on Silica Surfaces

Surface activation of the silica surface was achieved by immersing the silica substrates in a Piranha solution (3 H$_2$SO$_4$:1 H$_2$O$_2$ (30%)) over a period of 15 minutes. The substrates were subsequently thoroughly rinsed with water and conditioned in ethanol, positioned in polypropylene Petri dishes (100x100) mm and contacted with an R-silane/EtOH solution (2 mM) or an R'-silane/EtOH solution (2 mM) under moderate agitation over a period of 3 hours. In an embodiment of the present disclosure, the R-silane or R'-silane is (EtO)$_3$Si—R, (EtO)$_3$Si—R'. The functionalized substrates were then rinsed and stored in ethanol. A suspension (10 mL) of functionalized fluorescent core-shell particles, functionalized substrate surface, freshly prepared mM copper sulfate solution (4 mL; 5 mM) and ascorbic acid solution (80% ethanol, 1 mL; 5 mM) were mixed and left to react under agitation over various periods of time, ranging from 1 to 16 hours, and then rinsed several times with ethanol and water in a sonication bath.

Cardiac Fibroblasts Culture

Human (WT) and mouse (P2Y2R) valve interstitial cells were isolated by collagenase digestion (Jackson Laboratory, USA). Aortic valves from mice were dissected under a stereo microscope (Zeiss, ON, Canada) and pooled together (n=10) in order to start a culture. Cells were incubated with Dubelcco's Modified Eagle Medium (DMEM) and 10% fetal bovine serum (FBS), 1% sodium pyruvate and 1% glutamate.

The culture medium used during in vitro analysis was a conventional ringer buffer containing glucose (5 mM), potassium gluconate (5 mM), calcium gluconate (1 mM), magnesium sulfate (1 mM), sodium phosphate monobasic (2.5 mM), sodium bicarbonate (25 mM), HEPES (10 mM) and sodium gluconate (140 mM). Typical pH values for this solution were about 7.40.

Characterization Methods

Nanoparticle suspensions were analyzed by UV-visible spectrophotometry (Cary 50), transmission electronic microscopy (TEM; Tecnai G2 Spirit Biotwin), and scanning electron microscopy (SEM; Quanta 3D FEG). Characterization of the functionalized and grafted surfaces was achieved by UV-visible spectroscopy and microscopy (BX-53, Olympus) and by spectrofluorimetry (Jobin Yvon Fluorolog 3-22 equipped with a PMT R928 detector, Horiba). Microfluidic flow cells were assembled from the NP-grafted coverslip and a clean microscope slide, glued so as to set them at a controlled distance from each other, as well as two injection needles used as inlet and outlet ports. An epifluorescence microscope (Eclipse TE2000-5, Nikon) equipped with an enclosed chamber for controlled temperature (37° C.) and $CO_2$ concentration (5%) was used for cellular measurements.

Control flow cytometry measurements were performed using an appropriate volume of potassium phosphate buffer for each pH, with an addition of nigericin (proton uniporter blocker) for a final concentration of 10 µM. Fluorescent fibroblasts, by treatment with 2,7-bis(2-carboxyethyl)-5,6-carboxyfluorescein (BCECF), were suspended in these samples and kept on ice over a period of 1 minute and analysed by calculating the 530 nm (BCECF) and 600 nm (correction) ratiometry.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Webb, B. A.; Chimenti, M.; Jacobson, M. P.; Barber, D. L. *Deregulated pH: a perfect storm for cancer progression*, Nat Rev Cancer, 2011, 11: 671-677.
2. Geinberger, C.; Konnerth, A. *Imaging calcium in neurons*, Neuron, 2012, 73: 862-885.
3. Cash, K. J; Clark, H. A. *Phosphorescent nanosensors for in vivo tracking of histamine levels*, Anal Chem, 2013, 85: 6312-6318.
4. Lacroix, J. J.; Campos, F. V.; Frezza, L.; Bezanilla, F. *Molecular bases for the asynchronous activation of sodium and potassium channels required for nerve impulse generation*, Neuron, 2013, 79: 651-657.
5. O'Leary, M. E.; Hancox, J. C. *Role of voltage-gated sodium, potassium and calcium channels in the development of cocaine-associated cardiac arrhythmias*, Br J Clin Pharmacol, 2010, 69: 427-442.
6. Harjes, D. I.; Dubach, M.; Rosenzweig, A.; Das, S.; Clark, H. A. *Ion-selective optodes measure extracellular potassium flux in excitable cells*, Macromol Rapid Commun, 2010, 31: 217-221.
7. Yang W.; Wong, Y.; Ng, O. T. W.; Bai, L.-P.; Kwong, D. W. J.; Ke, Y.; Jiang, Z.-H.; Li, H.-W.; Yung, K. K. L.; Wong, M. S. *Inhibition of beta-amyloid peptide aggregation by multifunctional carbazole-based fluorophores*, Angew Chem Int Ed, 2012, 51: 1804-1810.
8. Bradburne, C. E.; Delehanty, J. B.; Gemmill, K. B.; Mei, B. C.; Mattoussi, H.; Susumu, K.; Blanco-Canosa, J. B.; Dawson, P. E.; Medintz, I. L. *Cytotoxicity of quantum dots used for in vitro cellular labeling: role of QD surface ligand, delivery modality, cell type, and direct comparison to organic fluorophores*, Bioconjugate Chem, 2013, 24: 1570-1583.
9. Lakowicz, J. R.; *Radiative decay engineering 5: metal-enhanced fluorescence and plasmon emission*, Anal Biochem, 2005, 337: 171-194.
10. Asian, K.; Gryczynski, I.; Malicka, J.; Maveeva, E.; Lakowicz, J. R.; Geddes, C. D. *Metal-enhanced fluorescence: an emerging tool in biotechnology*, Curr Opin Chem Biol, 2005, 16: 55-62.
11. Lee, K.; Hahn, L. D.; Yuen, W. W.; Vlamakis, H.; Kolter, R.; Mooney, D. J., *Metal-enhanced fluorescence to quantify bacterial adhesion*, Adv Mater, 2011, 23: H101-H104.
12. Viger, M. L.; Live, L. S.; Therrien, O. D.; Boudreau, D. *Reduction of self-quenching in fluorescent silica-coated silver nanoparticles*, Plasmonics, 2008, 3: 33-40.
13. Yang, J.; Zhang, F.; Chen, Y.; Qian, S.; Hu, P.; Li, W.; Deng, Y.; Fang, Y.; Han, L.; Luqman, M.; Zhao, D. *Core-shell $Ag@SiO_2@mSiO_2$ mesoporous nanocarriers for metal-enhanced fluorescence*, Chem Commun, 2011, 47: 11681-11620.
14. Rainville, L.; Dorais, M.-C.; Boudreau, D. *Controlled synthesis of low polydispersity $Ag@SiO_2$ core-shell nanoparticles for use in plasmonic applications*, RSC Adv, 2013, 3: 13953-13960.
15. Magnan, F.; Gagnon, J.; Fontaine, F.-G.; Boudreau, D. *Indium@silica core-shell nanoparticles as plasmonic enhancers of molecular luminescence in the UV region*, Chem Commun, 2013, 49: 9299-9301.
16. Brouard, D.; Ratelle, 0.; Bracamonte, A. G.; St-Louis, M.; Boudreau, D. *Direct molecular detection of SRY gene from unamplified genomic DNA by metal-enhanced fluorescence and FRET*, Anal Methods, 2013, 5: 6896-6899.
17. Bai, Z.; Chen, R.; Si, P.; Huang, Y.; Sun, H.; Kim, D.-H. *Fluorescent pH sensor based on $Ag@SiO_2$ core-shell nanoparticle*, ACS Appl Mater Interfaces, 2013, 5: 5856-5860.
18. Nath, N.; Chilkoti, A. *A colorimetric gold nanoparticle sensor to interrogate biomolecular interactions in real time on a surface*, Anal Chem, 2002, 74: 504-509.
19. Lin, P.-C.; Ueng, S.-H.; Yu, S.-C.; Jan, M.-D.; Adak, A. K.; Yu, C.-C.; Lin, C.-C. *Surface modification of magnetic* nanoparticles via a Cu(I)-catalyzed alkyne-azide cycloaddition, Org Lett, 2007, 9: 2131-2134.
20. Lin, P.-C.; Ueng, S.-H.; Tseng, M.-C.; Ko, J.-L.; Huang, K.-T.; Yu, S.-C.; Adak, A. K.; Chen, Y.-J.; Lin, C.-C. Site-specific protein modification through $Cu^I$-catalyzed 1,2,3-triazole formation and its implementation in protein microarray fabrication, Angew Chem Int Ed, 2006, 45: 4286-4290.
21. Fried, D. I.; Schlossbauer, A.; Bein, T. Immobilizing glycopyranose on mesoporous silica via "click-chemistry" for borate adsorption, Micropor Mesopor Mater, 2012, 147: 5-9.
22. Chandran, S. P.; Hotha, S.; Prasad, B. L. V. Tunable surface modification of silica nanoparticles through 'click' chemistry, Curr Sci, 2008, 95: 1327-1333.
23. Prakash, S.; Long, T. M.; Selby, J. C.; Moore, J. S.; Shannon, M. A. "Click" modification of silica surfaces and glass microfluidic channels, Anal Chem, 2007, 79: 1661-1667.
24. Viger, M. L.; Brouard, D.; Boudreau, D. Plasmon-enhanced resonance energy transfer from a conjugated polymer to fluorescent multilayer core-shell nanoparticles: a photophysical study, J Phys Chem C, 2011, 115: 2974-2981.
25. Deng, W.; Jin D.; Drozdowicz-Tomsia, K.; Yuan, J.; Wu, J.; Goldys, E. M. Ultrabright Eu-doped plasmonic $Ag@SiO_2$ nanostructures: time-gated bioprobes with single particle sensitivity and negligible background, Adv Mater, 2011, 23: 4649-4654.
26. Tovmchenko, O. G.; Graf, C.; van den Heuvel, D. J.; van Blaaderen, A.; Gerritsen, H. C. Fluorescence enhancement by metal-core/silica-shell nanoparticles, Adv Mater, 2006, 18: 91-95.
27. Devaraj, N. K.; Collman, J. P. Copper catalyzed azide-alkyne cycloadditions on solid surfaces: applications and future directions, QSAR Comb Sci, 2007, 11-12: 1253-1260.
28. Huang, L.; Dolai, S.; Raja, K.; Kruk, M. "Click" grafting of high loading of polymers and monosaccharides on surface of ordered mesoporous silica, Langmuir, 2010, 26: 2688-2693.
29. Rostovtsev, V. V.; Green, L. G.; Fokin, V. V.; Sharpless, K. B. A stepwise Huisgen cycloaddition process: copper (I)-catalyzed regioselective "ligation" of azides and terminal alkynes, Angew Chem, 2002, 114: 2708-2711.
30. Rodionov, V. O.; Fokin, V. V.; Finn, M. G. Mechanism of the ligand-free Cu(I)-catalyzed azide-alkyne cycloaddition reaction, Angew Chem, 2005, 117: 2250-2255.
31. Tian, Y.; Fuller, E.; Klug, S.; Lee, F.; Su, F.; Zhang, L.; Chao, S.-H.; Meldrum, D. R. A fluorescent colorimetric pH sensor and the influences of matrices on sensing performances, Sensor Actuat B-Chem, 2013, 188: 1-10.
32. Wieder, E. D.; Hang, H.; Fox, M. H. Measurement of intracellular pH using flow cytometry with carboxy-SNARF-1, Cytometry, 1993, 14: 916-921.
33. Klonis, N.; Sawyer, W. H. Spectral properties of the prototropic forms of the fluorescein in aqueous solution, J Fluoresc, 1996, 6: 147-157.
34. Nakata, E.; Nazumi, Y.; Yukimachi, Y.; Uto, Y.; Maezawa, H.; Hashimoto, T.; Okamoto, Y.; Hori, H. Synthesis and photophysical properties of new SNARF derivatives as duel emission pH sensors, Bioorg Med Chem Lett, 2011, 21: 1663-1666.
35. Tiedemann, D.; Taylor, U.; Rehbock, C.; Jakobi, J.; Klein, S.; Kues, W. A.; Barcikowski, S.; Rath, D. Reprotoxicity of gold, silver, and gold-silver allow nanoparticles on mammalian gametes, Analyst, 2014, 139: 931-942.
36. Leclerc, C.; Wilkinson, K. L. Bioaccumulation of nanosilver by Chlamydomonas reinhardtii—nanoparticle or the free ion?, Environ Sc Technol, 2014, 48: 358-364.
37. Franck, P.; Petitipain, N.; Cherlet, M.; Dardennes, M.; Maachi, F.; Schutz, B.; Poisson, L.; Nabet, P. Measurement of intracellular pH in cultured cells by flow cytometry with BCECF-AM, J Biotechnol, 1996, 46: 187-195.

TABLE 1

Non-limiting examples of R and R' groups capable of participating in a "click" cycloaddition reaction and resulting cycloadducts.

| R | R' | Cycloadduct |
| --- | --- | --- |
| R≡≡H | N≡N⁺—N⁻—R' | R-pyrazole-N—R' |
| R≡≡N | N≡N⁺—N⁻—R' | R-tetrazole-N—R' |
| R≡≡N⁺—O⁻ | R''≡≡R' | R,R''-isoxazole-R' |
| R—O—CH=CH₂ | HO-CH₂-naphthalene-diol—R' | R—O-chromane-naphthalene—R' |

TABLE 1-continued

Non-limiting examples of R and R' groups capable of participating in a "click" cycloaddition reaction and resulting cycloadducts.

| R | R' | Cycloadduct |
|---|----|-------------|
| (diene structure with R) | (alkene structure with R') | (cyclohexene with R and R') |

TABLE 2

Non-limiting examples of fluorescent ionophores and associated ions.

| Fluorescent Ionophore | Ion Selectivity |
|---|---|
| Oregon Green ™ | $Ca^{2+}$ |
| SBFI | $Na^+$ |
| PBFI | $K^+$ |
| Fura Red ™ | $Ca^{2+}$ |
| CoroNa ™ Green | $Na^+$ |
| FluoZin ™ | $Zn^{2+}$ |
| Newport Green ™ | $Ca^{2+}$ |
| Calcium Green ™ | $Ca^{2+}$ |
| Fluo-3 | $Ca^{2+}$ |
| Magnesium Green ™ | $Mg^{2+}$ |
| Calcium Orange ™ | $Ca^{2+}$ |
| Calcium Crimson ™ | $Ca^{2+}$ |
| TSQ | $Zn^{2+}$ |
| SNARF ™ | $H^+$ |
| MQAE | $Cl^-$ |
| Phen Green ™ | $Cu^{2+}$, $Cu^+$, $Fe^{2+}$, $Hg^{2+}$, $Pb^{2+}$, $Cd^{2+}$, $Zn^{2+}$, $Ni^{2+}$ |
| SPQ | $Cl^-$ |
| DNA aptamer | ATP (and other neurotransmitters) |

The invention claimed is:

1. A fluorescent sensor for extracellular ion concentration measurements, the fluorescent sensor comprising a photoluminescent nanostructure covalently grafted on a substrate surface, wherein the sensor emits a fluorescence emission in function of the extracellular ion concentration,
    wherein the photoluminescent nanostructure comprises a functionalized fluorescent metallic core-silica shell containing nanoparticle,
    wherein the substrate surface comprises a functionality complementary to the functionalized fluorescent metallic core-silica shell containing nanoparticle for covalent grafting of the photoluminescent nanostructure onto the substrate, and
    wherein the silica shell is functionalized with a first functionalized silane reagent having a first functionality, wherein the substrate surface is functionalized with a second functionalized silane reagent comprising a second functionality, and wherein the first and second functionalities undergo a cycloaddition reaction resulting in the covalent grafting of the photoluminescent nanostructure on the substrate.

2. The fluorescent sensor of claim 1, wherein the fluorescent silica shell comprises a fluorophore dispersed therein.

3. The fluorescent sensor of claim 1, wherein the photoluminescent nanostructure comprises a spacer shell interposed between the metallic core and the fluorescent silica shell, and wherein the fluorescent silica shell comprises a fluorophore dispersed therein.

4. The fluorescent sensor of claim 1, wherein the cycloaddition reaction is selected from [4+2] cycloadditions and [3+2] cycloadditions.

5. The fluorescent sensor of claim 1, wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

6. The fluorescent sensor of claim 1, wherein the ion is selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

7. The fluorescent sensor of claim 1, wherein the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh.

8. The fluorescent sensor of claim 1, wherein the substrate includes microarrays, beads, optical fibres, glass, modified or functionalized glass, quartz, mica, Si, $SiO_2$, modified silicon, thermoplastic polymers, polyvinyl alcohol, cellulose, paper and $TiO_2$.

9. The fluorescent sensor of claim 1, wherein the extracellular ion concentration measurement is an extracellular pH measurement, and wherein the sensor emits a fluorescence emission in function of the extracellular pH.

10. The fluorescent sensor of claim 1, wherein the substrate is a fiber, a bead, or a microarray.

11. The fluorescent sensor of claim 1, wherein the substrate has a flat surface.

12. The fluorescent sensor of claim 1, wherein the metal core is a plasmonic metal core.

13. The fluorescent sensor of claim 1, wherein the florescent sensor is in contact with the biological cell.

14. The fluorescent sensor of claim 13, wherein the biological cell is a eukaryote cell.

15. A method of detecting an extracellular ion concentration in a biological cell of a subject, the method comprising:
    contacting the fluorescent sensor of claim 1 with the biological cell; and
    measuring a fluorescence emission in function of the concentration of the ion concentration in the biological cell.

16. The method of claim 15, wherein the biological cell is a eukaryote cell.

17. A fluorescent sensor for multiplex extracellular ion concentration measurements, the fluorescent sensor comprising at least two distinct photoluminescent nanostructures covalently grafted on a substrate surface, wherein each of the distinct photoluminescent nanostructures emits a fluorescence emission in response to a distinct extracellular ion concentration,
    wherein the at least two distinct photoluminescent nanostructures each comprise a functionalized fluorescent metallic core-silica shell containing nanoparticle, wherein the substrate surface comprises a functionality complementary to each of the functionalized fluorescent metallic core-silica shell containing nanoparticles for covalent grafting of each of the at least two distinct photoluminescent nanostructures onto the substrate, and wherein the silica shell of at least one of the two distinct photoluminescent nanostructures is functionalized with a first functionalized silane reagent having a first functionality, wherein the substrate surface is functionalized with a second functionalized silane reagent comprising a second functionality, and wherein the first and second functionalities undergo a cycloaddition reaction resulting in the covalent grafting of the at least one of the two distinct photoluminescent nanostructures on the substrate.

18. The fluorescent sensor of claim 17, wherein the fluorescent silica shell comprises a fluorophore dispersed therein.

19. The fluorescent sensor of claim 18, wherein the distinct photoluminescent nanostructures further comprise a spacer shell interposed between the metallic core and the fluorescent silica shell.

20. The fluorescent sensor of claim 17, wherein the first and second functionalized silane reagents have a general formula independently chosen from $(R^1O)_3Si$—R or $(R^1O)_3Si$—R', wherein $R^1$ is an alkyl group and wherein R and R' are complementary groups comprising a functionality such that R and R' are capable of forming a cycloadduct resulting in the grafting of the nanoparticle on the substrate.

21. The fluorescent sensor of claim 17, wherein the cycloaddition reaction is selected from [4+2] cycloadditions and [3+2] cycloadditions.

22. The fluorescent sensor of claim 17, wherein the multiplex extracellular ions are independently selected from $H^+$, $Ca^{2+}$, $Na^+$, $K^+$, $Zn^{2+}$, $Mg^{2+}$, $Cl^-$, $Cu^{2+}$, $Cu^+$, $Fe^{2+}$, $Hg^{2+}$, $Pb^{2+}$, $Cd^{2+}$, $Zn^{2+}$ and $Ni^{2+}$.

23. The fluorescent sensor of claim 17, wherein the metallic core is selected from Si, Ni, Rh, Ir, Ni, Pd, Pt, Cu, Ag, Au, Zn, Cd, Ga, In, Tl, Ge, Sn, Ti, Zr, V, Nb, Cr, Mo, Mn, Tc, Fe, Ru and Rh.

24. The fluorescent sensor of claim 17, wherein the substrate includes microarrays, beads, optical fibres, glass, modified or functionalized glass, quartz, mica, Si, $SiO_2$, modified silicon, thermoplastic polymers, polyvinyl alcohol, cellulose, paper, or $TiO_2$.

25. The fluorescent sensor of claim 17, wherein the florescent sensor is in contact with the biological cell.

26. The fluorescent sensor of claim 25, wherein the biological cell is a eukaryote cell.

* * * * *